US009976177B2

(12) United States Patent
Terbrueggen

(10) Patent No.: US 9,976,177 B2
(45) Date of Patent: May 22, 2018

(54) CHEMICAL LIGATION DEPENDENT PROBE AMPLIFICATION (CLPA)

(75) Inventor: Robert Terbrueggen, Manhattan Beach, CA (US)

(73) Assignee: DXTERITY DIAGNOSTICS INCORPORATED, Rancho Dominguez, CA (US)

( * ) Notice: Subject to any disclaimer, the term of this patent is extended or adjusted under 35 U.S.C. 154(b) by 1378 days.

(21) Appl. No.: 12/798,108

(22) Filed: Mar. 29, 2010

(65) Prior Publication Data

US 2010/0267585 A1  Oct. 21, 2010

Related U.S. Application Data

(60) Provisional application No. 61/165,839, filed on Apr. 1, 2009.

(51) Int. Cl.
  C12Q 1/68   (2018.01)
  C12P 19/34  (2006.01)
  C07H 21/04  (2006.01)

(52) U.S. Cl.
  CPC ......... *C12Q 1/6855* (2013.01); *C12Q 1/6862* (2013.01)

(58) Field of Classification Search
  None
  See application file for complete search history.

(56) References Cited

U.S. PATENT DOCUMENTS

| | | |
|---|---|---|
| 4,469,863 A | 9/1984 | Ts'o et al. |
| 5,034,506 A | 7/1991 | Summerton et al. |
| 5,185,243 A | 2/1993 | Ullman et al. |
| 5,216,141 A | 6/1993 | Benner |
| 5,235,033 A | 8/1993 | Summerton et al. |
| 5,346,994 A | 9/1994 | Chomczynski |
| 5,386,023 A | 1/1995 | Sanghvi et al. |
| 5,476,930 A | 12/1995 | Letsinger et al. |
| 5,514,546 A | 5/1996 | Kool |
| 5,602,240 A | 2/1997 | De Mesmaeker |
| 5,637,684 A | 6/1997 | Cook et al. |
| 5,644,048 A | 7/1997 | Yau |
| 5,674,683 A | 10/1997 | Kool |
| 5,681,943 A | 10/1997 | Letsinger et al. |
| 5,683,874 A | 11/1997 | Kool |
| 5,714,320 A | 2/1998 | Kool |
| 5,780,613 A | 7/1998 | Letsinger et al. |
| 5,808,036 A | 9/1998 | Kool |
| 6,077,668 A | 6/2000 | Kool |
| 6,140,480 A | 10/2000 | Kool |
| 6,218,108 B1 | 4/2001 | Kool |
| 6,265,166 B1 | 7/2001 | Frank-Kamenetskii et al. |
| 6,479,650 B1 | 11/2002 | Kool |
| 6,511,810 B2 | 1/2003 | Bi et al. |
| 6,670,193 B2 | 12/2003 | Kool |
| 6,942,771 B1 | 9/2005 | Kayyem |
| 6,955,901 B2 | 10/2005 | Schouten |
| 7,033,753 B1 | 4/2006 | Kool |
| 7,153,658 B2 | 12/2006 | Anderson et al. |
| 7,198,900 B2 | 4/2007 | Woudenberg et al. |
| 2004/0110134 A1 | 6/2004 | Wenz et al. |
| 2004/0214196 A1 | 10/2004 | Aydin |
| 2004/0235005 A1 | 11/2004 | Friedlander et al. |
| 2004/0235154 A1 | 11/2004 | Oh et al. |
| 2004/0259102 A1 | 12/2004 | Kool |
| 2004/0259105 A1 | 12/2004 | Fan et al. |
| 2005/0142545 A1 | 6/2005 | Conn et al. |
| 2005/0208503 A1 | 9/2005 | Yowanto et al. |
| 2005/0208543 A1 | 9/2005 | Vann et al. |
| 2005/0272071 A1 | 12/2005 | Lao et al. |
| 2006/0003351 A1 | 1/2006 | Karger et al. |
| 2006/0024731 A1* | 2/2006 | Barany et al. ............. 435/6 |
| 2006/0063163 A1 | 3/2006 | Chen et al. |
| 2006/0068378 A1 | 3/2006 | Mirkin et al. |
| 2006/0199192 A1* | 9/2006 | Kool et al. ............ 435/6 |
| 2007/0072821 A1 | 3/2007 | Iakouboya et al. |
| 2007/0218477 A1* | 9/2007 | Thomas ................... 435/6 |
| 2008/0124810 A1 | 5/2008 | Terbrueggen |

(Continued)

FOREIGN PATENT DOCUMENTS

| | | |
|---|---|---|
| EP | 320308 | 6/1989 |
| EP | 439182 | 7/1991 |
| EP | 1130113 A1 | 9/2001 |

(Continued)

OTHER PUBLICATIONS

"Viruses" (Wikipedia.com, accessed Nov. 24, 2012).*
"How many species of bacteria are there" (wisegeek.com; accessed Sep. 23, 2011).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
Abe et al., "Destabilizing Universal Linkers for Signal Amplification in Self-Lighting Probes for RNA" *J. Am. Chem. Soc.* (2004) 126:13980:13986.

(Continued)

*Primary Examiner* — Bradley L Sisson

(74) *Attorney, Agent, or Firm* — Morgan, Lewis & Bockius LLP; Robin M. Silva

(57) ABSTRACT

The present invention provides compositions, apparatuses and methods for detecting one or more nucleic acid targets present in a sample. Methods of the invention include utilizing two or more oligonucleotide probes that reversibly bind a target nucleic acid in close proximity to each other and possess complementary reactive ligation moieties. When such probes have bound to the target in the proper orientation, they are able to undergo a spontaneous chemical ligation reaction that yields a ligated oligonucleotide product. In one aspect, the ligation product is of variable length that correlates with a particular target. Following chemical ligation, the probes may be amplified and detected by capillary electrophoresis or microarray analysis.

12 Claims, 8 Drawing Sheets

(56) References Cited

U.S. PATENT DOCUMENTS

| | | | |
|---|---|---|---|
| 2010/0267585 | A1 | 10/2010 | Terbrueggen |

FOREIGN PATENT DOCUMENTS

| | | |
|---|---|---|
| WO | WO 1989/012696 | 12/1989 |
| WO | WO 1990/001069 | 2/1990 |
| WO | WO 1992/020702 | 11/1992 |
| WO | WO 1994/024143 A1 | 10/1994 |
| WO | WO 1994/029485 | 12/1994 |
| WO | WO 1995/015971 | 6/1995 |
| WO | WO 1996/035699 | 11/1996 |
| WO | WO 1996/040712 | 12/1996 |
| WO | WO 1997/031256 | 8/1997 |
| WO | WO 1997/046568 | 12/1997 |
| WO | WO 1998/020162 | 5/1998 |
| WO | WO 1999/037819 | 7/1999 |
| WO | WO 2001/027326 | 4/2001 |
| WO | WO 2001/092579 A2 | 12/2001 |
| WO | WO 2001/094638 | 12/2001 |
| WO | WO 2002/002823 | 1/2002 |
| WO | WO 2004/005545 A1 | 1/2004 |
| WO | WO 2004/076692 | 9/2004 |
| WO | WO 2007/133703 | 11/2007 |
| WO | WO 2010/114599 | 10/2010 |

OTHER PUBLICATIONS

Abe et al., "Flow cytometric detection of specific RNAS in native human cells with quenched autoligating FRET probes" *Proc. Natl. Acad. Sci. USA* (2006) 103(2):263-8.
Abramson et al., "Nucleic acid amplification technologies" *Current Opinion in Biotechnology* (1993) 4:41-47.
Arar et al., "Synthesis and Antiviral Activity of Peptide-Oligonucleotide Conjugates Prepared by Using $N_\alpha$(Bromoacetyl) peptides" *BioConj. Chem.* (1995) 6:573.
Bachmann et al., "Improvement of PCR amplified DNA sequencing with the aid of detergents" *Nucleic Acid Res.* (1990) 18:1309.
Backes et al., "An Alkanesulfonamide 'Safety-Catch' Linker for Solid-Phase Synthesis" *J. Org. Chem.* 64:2322-2330.
Baselt, D.R. et al., "A Biosensor Based on Magnetoresistance Technology", *Biosensors & Bioelectronics,* (1998) 13:731-739.
Beaucage et al., "The Functionalization of Oligonucleotides Via Phosphoramidite Derivatives" *Tetrahedron* (1993) 49(10):1925.
Bibikova, M. et al., "Quantitative Gene Expression Profiling in Formalin-Fixed, Paraffin-Embedded Tissues Using Universal Bead Arrays", *American Journal of Pathology,* (2004) 165:5 1799-1807.
Botti et al., "Chemical Synthesis of Proteins and Circular Peptides Using $N^\alpha$-1(1-Phenyl-2-Mercaptoethyl) Auxiliaries" *Protein Pept. Lett.* (2005) 12(8):729-35.
Brill et al., "Synthesis of Oligodeoxynucleoside Phosphorodithioates via Thioamidites" *J. Am. Chem. Soc.* (1989) 111:2321.
Carlsson et al., "Screening for genetic mutations" *Nature* (1996) 380:207.
Chan et al., "Construction and Characterization of a Heterodimeric Iron Protein: Defining Roles for Adenosine Triphosphate in Nitrogenase Catalysis" *Biochemistry* (2000) 39(24):7221-8.
Cuppolletti et al., "Oligomeric Fluorescent Labels for DNA" *Bioconjug. Chem.* (2005) 16(3):528-34.
Dempcy et al., "Synthesis of a thymidyl pentamer of deoxyribonucleic guanidine and binding studies with DNA homopolynucleotides" *Proc. Natl. Acad. Sci. USA* (1995) 92:6097.
Dill, K. et al., "Immunoassays and Sequence-Specific DNA Detection on a Microchip Using Enzyme Amplified Electrochemical Detection", *J. Biochem. Biophys. Methods,* (2004) 59:181-187.
Dogan et al., "5'-Tethered Stilbene Derivatives as Fidelity-and Affinity-Enhancing Modulators of DNA Duplex Stability" *J. Am. Chem. Soc.* (2004) 126:4762-4763.
Dose et al., "Convergent Synthesis of Peptide Nucleic Acids by Native Chemical Ligation", *Org. Letters* (2005) 7:20 4365-4368.

Dose et al., "Reducing Product Inhibition in DNA-Template-Controlled Ligation Reactions", *Agnew. Chem. Int. Ed.* (2006) 45:5369-5373.
Egholm, M. et al., "Peptide Nucleic Acids (PNA). Oligonucleotide Analogues with an Achiral Peptide Backbone" *J. Am. Chem. Soc.* (1992) 114:1895.
Egholm, M. et al. "PNA Hybridizes to Complementary Oligonucleotides Obeying the Watson-Crick Hydrogen-Bonding Rules", *Nature,* (1993) 365:566-568.
Fan, JB et al., "A Versatile Assay for High-Throughput Gene Expression Profiling on Universal Array Matrices", *Genome Research,* (2004) 14, 878-885.
Ficht et al., "Single-Nucleotide-Specific PNA-Peptide Ligation on Synthetic and PCR DNA Templates", *J. Am. Chem. Soc.* (2004) 126:9970-9981.
Ficht et al. "As Fast and Selective as Enzymatic Ligations: Unpaired Nucleobases Increase the Selectivity of DNA-Controlled Native Chemical PNA Ligation" *ChemBioChem* (2005) 6:2098-2103.
Foss, R.D. et al., "Effects of Fixative and Fixation Time on the Extraction and Polymerase Chain Reaction Amplification of RNA from Paraffin-Embedded Tissue. Comparison of Two Housekeeping Gene mRNA Controls", *Diagn. Mol. Pathol.,* 3(3):148-155 (1994).
Gottesfeld, J.M. et al., "Sequence-specific Recognition of DNA in the Nucleosome by Pyrrole-Imidazole Polyamides" *J. Mol. Biol.* (2001) 309:615-629.
Grossmann et al., "DNA-Catalyzed Transfer of a Reporter Group" *J. Am. Chem. Soc.* (2006) 128:15596-15597.
Gryaznov, S.M. and Letsinger, R.L., "Template controlled coupling and recombination of oligonucleotide blocks containing thiophosphoryl groups" *Nucleic Acids Research* (1993) 21:1403.
Gryaznov et al., "Chemical Ligation of Oligonucleotides in the Presence and Absence of Template", *J. Am. Chem. Soc.,* (1993) 115(9):3808-3809.
Gryaznov et al., "Enhancement of Selectivity in Recognition of Nucleic Acids via Chemical Autoligation", *Nucleic Acids Res.,* (1994) 22:2366-2369.
Herrlein and Letsinger, "A Covalent Lock for Self-Assembled Oligonucleotide Conjugates", *J. Am. Chem. Soc.,* (1995) 117:10151-10152.
Horn et al., "Oligonucleotides with Alternating Anionic and Cationic Phosphoramidate Linkages: Synthesis and Hybridization of Sterio-uniform Isomers", *Tetrahedron Letters* (1996) 37:743.
Jeffs et al., "Unusual conformation of a 3'-thioformacetal linkage in a DNA duplex" *J. Biomolecular NMR* (1994) 34:17.
Jenkins et al., "The Biosynthesis of Carbocyclic Nucleosides" *Chem. Soc. Rev.* (1995) pp. 169-176.
Kenner, G.W., "The Safety Catch Principle in Solid Phase Peptide Synthesis", *J. Chem. Soc.* (1971) pp. 636-637.
Kiedrowski et al., "Parabolic Growth of a Self-Replicating Hexadeoxynucleotide Bearing a 3'5'-Phosphoamidate Linkage" *Agnew. Chem. Intl. Ed.* English (1991) 30:423.
Kool, E.T. et al., "Convergent DNA synthesis: a non-enzymatic dimerization approach to circular oligodeoxynucleotides" *Nucleic Acid Res.* (1995) 23 (17):3547.
Koshkin et al., "LNA (Locked Nucleic Acid): An RNA Mimic Forming Exceeingly Stable LNA:LNA Duplexes" *J. Am. Chem. Soc.* (1998) 120:13252-3.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" *Tetrahedron* (1998) 54:3607-3630.
Kutyavin et al., "Oligonucleotides with conjugated dihydropyrroloindole tripeptides: base composition and backbone effects on hybridization" *Nucleic Acids Research* (1997) vol. 25, No. 18:3718-3723.
Kutyavin et al., "3'-Minor groove binder—DNA probes increase sequence specificity at PCR extension temperatures" *Nucleic Acids Research* (2000) vol. 28, No. 2:655-661.
Landegren, U. "Ligation-based DNA Diagnostics" *Bioessays* (1993) 15(11):761-5.
Landegren, U. et al., "A Ligase-Mediated Gene Detection Technique", *Science,* (1988) 241(4689):1077-1080.

(56) References Cited

OTHER PUBLICATIONS

Letsinger et al., "Phosphoramidate Analogs of Oligonucleotides" *J. Org. Chem.* (1970) 35:3800.
Letsinger et al., *Nucl. Acids Res.* (1986) 14:3487.
Letsinger et al., "Cationic Oligonucleotides" *J. Am. Chem. Soc.* (1988) 110:4470.
Letsinger et al., "Hybridization of Alternating Cationic/Anionic Oligonucleotides to RNA Segments", *Nucleotide and Nucleoside* (1994) 13:1597.
Liu, R. et al., "Fully Integrated Miniature Device for Automated Gene Expression DNA Microarray Processing", *Anal. Chem.,* (2006) 78(6):1980-1986.
Luebke and Dervan, "Nonenzymatic Sequence-Specific Ligation of Double-Helical DNA", *J. Am. Chem. Soc.,* (1991) 113:7447-7448.
Luebke, K.J. and Dervan, P.B., "Nonenzymatic Ligation of Oligodeoxyribonucleotides no a Duplex DNA Template by Triple-Helix Formation", *J. Am. Chem. Soc.* (1989) 111:8733.
Mag et al., "Synthesis and selective cleavage of an oligodeoxynucleotide containing a bridged internucleotide 5'-phosphorothioate linkage", *Nucleic Acids Res.* (1991) 19:1437-1441.
Marshall et al., "DNA Chips: An Array of Possibilities", *Nat Biotechnol.* (1998) 16(1):27-31.
Martel et al., (High Throughput Genomics) "Multiplex Screening Assay for mRNA Combining Nuclease Protection with Luminescent Array Detection," *Assay and Drug Development Technologies* 1:61-71 (2002).
Meier et al., "Peptide Nucleic Acids (PNAs)—Unusual Properties of Nonionic Oligonucleotide Analogues" *Chem. Int. Ed. Engl.* (1992) 31:1008.
Mesmaeker et al., "Comparison of Rigid and Flexible Backbones in Antisense Oligonucleotides", *Bioorganic & Medicinal Chem. Lett.* (1994) 4:395.
Metelev, V.G. et al., "Oligodeoxyribonucleotides With Internucleotidic or Terminal Phosphorothioate Groups: Different Pathways in the Reaction with Water-Soluble Carbodimide", *Nucleosides & Nucleotides* (1999) 18:2711.
Miller, G.P. et al., "New, stronger nucleophiles for nucleic acid-templated chemistry: Synthesis and application in fluorescence detection of cellular RNA", *Bioorganic and Medicinal Chemistry* (2008) 16:56-64.
Moran et al., "A thymidine triphospate shape analog lacking Watson-Crick pairing ability is replicated with high sequence selectivity", *Proc. Natl. Acad. Sci. USA* (1997) 94(20):10506-11.
Narayanan et al., "Clamping down on weak terminal base pairs: oligonucleotides with molecular caps as fidelity-enhancing elements at the 5'- and 3'-terminal residues", *Nucleic Acids Research* (2004) 32:2901-2911.
Nickerson, "Gene probe assays and their detection", *Current Opinion in Biotechnology* (1993) 4:48-51.
Nilsson, M. et al., "RNA-Templated DNA Litigation for Transcript Analysis", *Nucleic Acids Research,* 29:2 578-581 (2001).
Offer et al., "Extending Synthetic Access to Proteins with a Removable Acyl Transfer Auxiliary", *J. Am. Chem. Soc.* (2002) 124(17):4642-6.
Ollivier et al., "Fmoc Solid-Phase Synthesis of Peptide Thioesters Using an Intramolecular N,S-Acyl Shift" *Organic Letters* (2005) vol. 7, No. 13, pp. 2647-2650.
Pauwels et al., "Biological Activity of New 2-5A Analogues", *Chemica Scripta* (1986) 26:141.
Pooga, M. et al., "PNA oligomers as tools for specific modulation of gene expression", *Biomolecular Engineering* (2001) 17:183-192.
Pritchard et al., "Effects of Base Mismatches on Joining of Short Oligonucleotides by DNA Ligases", *Nucleic Acids Res.* (1997) 25(17):3403-7.
Rawls, R.,"Optimistic About Antisense "*C & E News* (Jun. 2, 1997), p. 35-39.
Sando et al., "Nonenzymatic DNA ligation in *Escherichia coli* cells", *Nucleic Acids Res. Suppl.* (2002) 2:121-2.
Sando et al., "Quencher as Leaving Group: Efficient Detection of DNA-Joining Reactions", *J. Am. Chem. Soc.* (2002) 124(10)2096-7.
Sando et al., "Imaging of RNA in Bacteria with Self-Ligating Quenched Probes", *Journal Am. Chem.* (2002) 124(33):9686-7.
Sando et al., "Quenched Auto-Ligating DNAs: Multicolor Identification of Nucleic Acids at Single Nucleotide Resolution", *J. Am. Chem. Soc.* (2004) 126(4):1081-7.
Sawai et al., "Synthesis and Properties of Oligoadenylic Acids Contaiing 2'-5' Phosphoramide Linkage", *Chem. Lett.* (1984) 805.
Schafer et al., "DNA variation and the future of human genetics", *Nature Biotechnology* (1993) 16:33-39.
Shabarova, Z.A., et al., "Chemical ligation of DNA: the first non-enzymatic assembly of a biologically active gene", *Nucleic Acids Research* (1991) 19:4247.
Silverman et al., "Quenched autoligation probes allow discrimination of live bacterial species by single nucleotide differences in rRNA", *Nucleic Acids Res.* (2005) 33(15):4978-86.
Silverman et al., "Detecting RNA and DNA with Templated Chemical Reactions", *Chem. Rev.,* (2006) 106:3775-3789.
Sprinzl et al., "Enzymatic Incorporation of ATP and CTP Analogues into the 3' End of Trna", *Eur. J. Biochem.* (1977) 81:579.
Steemers, F.J. et al., "Screening Unlabeled DNA Targets with Randomly Ordered Fiber-Optic Gene Arrays", *Nat Biotechnol.* (2000) 18(1):91-4.
Stetsenko and Gait, "Efficient Conjugation of Peptides to Oligonucleotides by 'Native Ligation'", *J. Org. Chem.* (2000) 65(16):4900-8.
Ueno, Y. et al., "Nucleosides and Nucleotides. 165. Chemical Ligation of Oligodeoxynucleotides Having a Mercapto Group at the 5-Position of 2'-Deoxyuridine Via a Disulfide Bond" Nucleosides and Nucleotides, Marcel Dekker Inc., vol. 17, No. 1-3 (1998) pp. 283-289.
Umek, R.M. et al., "Electronic Detection of Nucleic Acids—A Versatile Platform for Molecular Diagnostics", *J. Molecular Diagnostics,* (2001) 3:74-84.
van't Veer, L.J., et al., "Gene Expression Profiling Predicts Clinical Outcome of Breast Cancer", *Nature,* (2002) 415(6871):530-536 (2002).
Wahlestedt C. et al., "Potent and nontoxic antisense oligonucleotides containing locked nucleic acids", *PNAS* (2000) 97:5633-5638.
Wang et al., "Large-Scale Identification, Mapping, and Genotyping of Single-Nucleotide Polymorphisms in the Human Genome", *Science* (1998) 280:1077.
Warren et al., "Toward Fully Synthetic Glycoproteins by Ultimately Convergent Routs: A Solution to a Long-Standing Problem", *J. Am. Chem. Soc.* (2004) 126(21):6576-82.
Weizmann, Y. et al., "Magneto-Mechanical Detection of Nucleic Acids and Telomerase Activity in Cancer Cells", *J. Am. Chem. Soc.,* (2004) 126:1073-1080.
Wengel, J. et al., "LNA (Locked Nucleic Acid)", *Nucleosides & Nucleotides,* (1999) 18:1365-1370.
Wu, D.Y. et al., "The Ligation Amplification Reaction (LAR)—Amplification of Specific DNA Sequences Using Sequential Rounds of Template-Dependent Ligation", *Genomics* (1989) 4(4):560-9.
Xu et al., "Chemical and enzymatic properties of bridging 5'-S-phosphorothioester linkages in DNA", *Nucleic Acid Res.* (1998) 26(13):3159-64.
Xu et al., "Nonenzymatic Autoligation in Direct Three-Color Detection of RNA and DNA Point Mutations" *Nature Biotechnology* (2001) 19(2):148-52.
Xu and Kool, E.T., "A Novel 5'-Iodonucleoside Allows Efficient Nonenzymatic Ligation of Single-stranded and Duplex DNAs", *Tetrahedron Letters* (1997) 38:5595.
Xu and Kool, E.T., "High sequence fidelity in a non-enzymatic DNA autoligation reacation", *Nucleic Acid Research* (1999) 27:875.
Yang et al., "Badge, Beads Array for the Detection of Gene Expression, a High Throughput Diagnostic Bioassay", *Genome Research* (2001) 11(11):1888-98.
Yeakley, JM et al., "Profiling Alternative Splicing on Fiber-Optic Arrays", *Nature Biotechnology,* (2002) 20:353-358.

(56) References Cited

OTHER PUBLICATIONS

Castiglioni et al., "Development of a Universal Microarray Based on the Ligation Detection Reaction and 16S rRNA Gene Polymorphism to Target Diversity of Cyanobacteria", *Applied and Environmental Microbiology*, vol. 70, No. 12, pp. 7161-7172 (2004).

Grossman et al., "High-Density Multiplex Detection of Nucleic Acid Sequences: Oligonucleotide Ligation Assay and Sequence-Coded Separation", *Nucleic Acids Research*, Oxford University Press, Surrey, Great Britain, vol. 22, No. 21, pp. 4527-4534 (1994).

Karim et al., "Convenient genotyping of six myostatin mutation causeing double-muscling in cattle using a multiplex oligonucleotide ligation assay", *Animal Genetics*, vol. 31, No. 6, pp. 396-399 (2000).

Schouten et al., "Relative quantification of 40 nucleic acid sequences by multiplex ligation-dependent probe amplification", *Nucleic Acid Research*, Oxford University Press, Great Britain, vol. 30, No. 12 (2002).

Stern et al., "Multiplex ligation-dependent probe amplification using a completely synthetic probe set", *Biotechniques*, vol. 37, No. 3, pp. 399-405 (2004).

Van Eijk, M.J.T., "SNPWaveTM: a flexible multiplexed SNP genotyping technology", *Nucleic Acids Research*, vol. 32, No. 4 (2004).

\* cited by examiner

CPG = Control Pore Glass
DMT = bis-(4-methoxyphenyl)phenylmethyl

SEQUENCE LISTING

```
<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggttcccta agggttgga                                                    19

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgccagcaa gatccaatct aga                                               23

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tacatccttc ctagtcaatt acactctaga ttggatcttg ctggcac                     47
```

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gggttcccta agggttggat aggtaaatgg cagtgtagaa c                          41

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgtaattga ctaggaagga tgtagttcta cactgccatt taccta                    46

<210> SEQ ID NO 6
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guguaauuga cuaggaagga uguaguucua cacugccauu uaccua                    46

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tggtttggtg cttcaaatac tctctagatt ggatcttgct ggcac                     45

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gggttcccta agggttggat cgagtctaca gatccccaac tttcatagtc tgaaactttc     60
tcc                                                                   63

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agtatttgaa gcaccaaacc aggagaaagt ttcagactat ga                        42

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tagcagacac atccaggctc tagattggat cttgctggca c                41

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
gggttcccta agggttggat cgagtctact ccaactttga ccaccattcg gctac      55

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcctggatgt gtctgctagt agccgaatgg tggtca             36

<210> SEQ ID NO 13
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gccuggaugu gucugcuagu agccgaaugg ugguca             36

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
tccgagattt ccccctctag attggatctt gctggcac             38

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
gggttcccta agggttggat cccagactcc tccctct             37

-continued

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggggaaatc tcggaagagg gaggagtctg gg                                  32

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tcacggtctg ccacgctcta gattggatct tgctggcac                           39

<210> SEQ ID NO 18
<211> LENGTH: 53
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gggttcccta agggttggat gagtctacat gatccttccc gccacaaaga tgg           53

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgtggcagac cgtgaccatc tttgtggcgg ga                                  32

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
gggttcccta agggttggac ggacgcctgc ttcaccacct tcttgatgtc a             51

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tcatatttgg caggtttttc tagacggcag gt                                  32

```
<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
caggtccacc actgacacgt tggcagttct agattggatc ttgctggcac              50

<210> SEQ ID NO 23

<400> SEQUENCE: 23

000                                                                  3

<210> SEQ ID NO 24
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
actgccaacg tgtcagtggt ggacctgacc tgccgtctag aaaaacctgc caaatatgat   60
gacatcaaga aggtggtgaa gcaggcgtc                                     89

<210> SEQ ID NO 25
<211> LENGTH: 76
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ttttctagac ggcaggtcag gtccaccaga tgatcgacga gacactctcg ccatctagat   60
tggatcttgc tggcac                                                   76

<210> SEQ ID NO 26
<211> LENGTH: 79
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gggttcccta agggttggac ggaccaactc ctcgccatat catctgtaca ccttcttgat   60
gtcatcatat ttggcaggt                                                79

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ccaactcctc gccatatcat ctgtacacct tcttg                              35

<210> SEQ ID NO 28
```

```
<211> LENGTH: 78
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
tgctgatgat cttgaggctg ttgtcatact gatgatcgac gagacactct cgccatctag    60
attggatctt gctggcac                                                  78

<210> SEQ ID NO 29
<211> LENGTH: 75
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gggttcccta agggttggac gatggagttg atgctgacgg aagtcatagt aagcagttgg    60
tggtgcagga ggcat                                                     75

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
tgctgacgga agtcatagta agcagttggt                                     30

<210> SEQ ID NO 31
<211> LENGTH: 77
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tccttgagtg cctccaacac cttcttgagg atgatcgacg agacactctc gccatctaga    60
ttggatcttg ctggcac                                                   77

<210> SEQ ID NO 32
<211> LENGTH: 77
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
gggttcccta agggttggac ggtacaacaa gacccagctg acgactctta atatcccagc    60
aggcctcgtt gatgagg                                                   77

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 33
ctgacgactc ttaatatccc agcaggcctc gtt                               33

<210> SEQ ID NO 34
<211> LENGTH: 78
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
ttagttccaa gataaccttg gttccaggct gatgatcgac gagacactct cgccatctag  60
attggatctt gctggcac                                                78

<210> SEQ ID NO 35
<211> LENGTH: 79
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
gggttcccta agggttggac gttagacgcc aataggagtt tcactggtgg ctaccaccca  60
ctgagaggag aaaagtcat                                               79

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
cgccaatagg agtttcactg gtggctacca                                   30
```

CHEMICAL LIGATION DEPENDENT PROBE AMPLIFICATION (CLPA)

RELATED CASES

This application claims priority from U.S. Provisional Application No. 61/165,839, filed Apr. 1, 2009, whose entire disclosure is incorporated by this reference as though set forth fully herein.

The instant application contains a Sequence Listing which has been submitted via EFS-Web and is hereby incorporated by reference in its entirety. Said ASCII copy, created on May 13, 2010, is named 14441002.txt, and is 9,126 bytes in size.

FIELD OF THE INVENTION

This invention relates to compositions and methods for detecting nucleic acids in a sample using chemical ligation.

BACKGROUND OF THE INVENTION

This invention relates to compositions, apparatus and methods for detecting one or more nucleic acid targets present in a sample. The detection of specific nucleic acids is an important tool for diagnostic medicine and molecular biology research.

Gene probe assays currently play roles in identifying infectious organisms such as bacteria and viruses, in probing the expression of normal and mutant genes and identifying genes associated with disease or injury, such as oncogenes, in typing tissue for compatibility preceding tissue transplantation, in matching tissue or blood samples for forensic medicine, for responding to emergency response situations like a nuclear incident or pandemic flu outbreak, in determining disease prognosis or causation, and for exploring homology among genes from different species.

Ideally, a gene probe assay should be sensitive, specific and easily automatable (for a review, see Nickerson, *Current Opinion in Biotechnology* (1993) 4:48-51.) The requirement for sensitivity (i.e. low detection limits) has been greatly alleviated by the development of the polymerase chain reaction (PCR) and other amplification technologies which allow researchers to exponentially amplify a specific nucleic acid sequence before analysis (for a review, see Abramson et al., *Current Opinion in Biotechnology*, (1993) 4:41-47). For example, multiplex PCR amplification of SNP loci with subsequent hybridization to oligonucleotide arrays has been shown to be an accurate and reliable method of simultaneously genotyping hundreds of SNPs (see Wang et al., *Science*, (1998) 280:1077; see also Schafer et al., *Nature Biotechnology*, (1989)16:33-39).

Specificity also remains a problem in many currently available gene probe assays. The extent of molecular complementarity between probe and target defines the specificity of the interaction. Variations in composition and concentrations of probes, targets and salts in the hybridization reaction as well as the reaction temperature, and length of the probe may all alter the specificity of the probe/target interaction.

It may be possible under some circumstances to distinguish targets with perfect complementarity from targets with mismatches, although this is generally very difficult using traditional technology, since small variations in the reaction conditions will alter the hybridization. Newer techniques with the necessary specificity for mismatch detection include probe digestion assays in which mismatches create sites for probe cleavage, and DNA ligation assays where single point mismatches prevent ligation.

A variety of enzymatic and non-enzymatic methods are available for detecting sequence variations. Examples of enzyme based methods include Invader™, oligonucleotide ligation assay (OLA) single base extension methods, allelic PCR, and competitive probe analysis (e.g. competitive sequencing by hybridization). Enzymatic DNA ligation reactions are well known in the art (Landegren, *Bioessays* (1993) 15(11):761-5; Pritchard et al., *Nucleic Acids Res.* (1997) 25(17):3403-7; Wu et al., *Genomics,* (1989) 4(4): 560-9) and have been used extensively in SNP detection, enzymatic amplification reactions and DNA repair.

A number of non-enzymatic or template mediated chemical ligation methods have been developed that can be used to detect sequence variations. These include chemical ligation methods that utilize coupling reagents, such as N-cyanoimidazole, cyanogen bromide, and 1-ethyl-3-(3-dimethylaminopropyl)-carbodiimide hydrochloride. See Metelev, V. G., et al., *Nucleosides & Nucleotides* (1999) 18:2711; Luebke, K. J., and Dervan, P. B. *J. Am. Chem. Soc.* (1989) 111:8733; and Shabarova, Z. A., et al., *Nucleic Acids Research* (1991)19:4247, each of which is incorporated herein by reference in its entirety.

Kool (U.S. Pat. No. 7,033,753), which is incorporated herein by reference in its entirety describes the use of chemical ligation and fluorescence resonance energy transfer (FRET) to detect genetic polymorphisms. The readout in this process is based on the solution phase change in fluorescent intensity.

Terbrueggen (U.S. Patent application 60/746,897) which is incorporated herein by reference in its entirety describes the use of chemical ligation methods, compositions and reagents for the detection of nucleic acids via microarray detection.

Other chemical ligation methods react a 5'-tosylate or 5'-iodo group with a 3'-phosphorothioate group, resulting in a DNA structure with a sulfur replacing one of the bridging phosphodiester oxygen atoms. See Gryanov, S. M., and Letsinger, R. L., *Nucleic Acids Research* (1993) 21:1403; Xu, Y. and Kool, E. T. *Tetrahedron Letters* (1997) 38:5595; and Xu, Y. and Kool, E. T., *Nucleic Acids Research* (1999) 27:875, each of which is herein incorporated by reference in its entirety.

Some of the advantages of using non-enzymatic approaches for nucleic acid target detection include lower sensitivity to non-natural DNA analog structures, ability to use RNA target sequences, lower cost and greater robustness under varied conditions. Letsinger et al (U.S. Pat. No. 5,780,613, herein incorporated by reference in its entirety) have previously described an irreversible, nonenzymatic, covalent autoligation of adjacent, template-bound oligonucleotides wherein one oligonucleotide has a 5' displaceable group and the other oligonucleotide has a 3' thiophosphoryl group.

PCT applications WO 95/15971, PCT/US96/09769, PCT/US97/09739, PCT US99/01705, WO96/40712 and WO98/20162, all of which are expressly incorporated herein by reference in their entirety, describe novel compositions comprising nucleic acids containing electron transfer moieties, including electrodes, which allow for novel detection methods of nucleic acid hybridization.

One technology that has gained increased prominence involves the use of DNA arrays (Marshall et al., *Nat Biotechnol.* (1998) 16(1):27-31), especially for applications involving simultaneous measurement of numerous nucleic acid targets. DNA arrays are most often used for gene expression monitoring where the relative concentration of 1 to 100,000 nucleic acids targets (mRNA) is measured simultaneously. DNA arrays are small devices in which nucleic acid anchor probes are attached to a surface in a pattern that is distinct and known at the time of manufacture (Marshall et al., *Nat Biotechnol.* (1998) 16(1):27-31) or can be accurately deciphered at a later time such as is the case for bead arrays (Steemers et al., *Nat Biotechnol.* (2000) 18(1):91-4; and Yang et al., *Genome Res.* (2001) 11(11):1888-98.). After a series of upstream processing steps, the sample of interest is brought into contact with the DNA array, the nucleic acid targets in the sample hybridize to anchor oligonucleotides on the surface, and the identity and often concentration of the target nucleic acids in the sample are determined.

Many of the nucleic acid detection methods in current use have characteristics and/or limitations that hinder their broad applicability. For example, in the case of DNA microarrays, prior to bringing a sample into contact with the microarray, there are usually a series of processing steps that must be performed on the sample. While these steps vary depending upon the manufacturer of the array and/or the technology that is used to read the array (fluorescence, electrochemistry, chemiluminescence, magnetoresistance, cantilever deflection, surface plasmon resonance), these processing steps usually fall into some general categories: Nucleic acid isolation and purification, enzymatic amplification, detectable label incorporation, and clean up post-amplification. Other common steps are sample concentration, amplified target fragmentation so as to reduce the average size of the nucleic acid target, and exonuclease digestion to convert PCR amplified targets to a single stranded species.

The requirement of many upstream processing steps prior to contacting the DNA array with the sample can significantly increase the time and cost of detecting a nucleic acid target(s) by these methods. It can also have significant implications on the quality of the data obtained. For instance, some amplification procedures are very sensitive to target degradation and perform poorly if the input nucleic acid material is not well preserved (Foss et al., *Diagn Mol Pathol.* (1994) 3(3):148-55). Technologies that can eliminate or reduce the number and/or complexity of the upstream processing steps could significantly reduce the cost and improve the quality of results obtained from a DNA array test. One method for reducing upstream processing steps involves using ligation reactions to increase signal strength and improve specificity.

There remains a need for methods and compositions for efficient and specific nucleic acid detection. Accordingly, the present invention provides methods and compositions for non-enzymatic chemical ligation reactions which provides very rapid target detection and greatly simplified processes of detecting and measuring nucleic acid targets.

SUMMARY OF THE INVENTION

Accordingly, in one aspect, the invention relates to a method comprising providing a ligation substrate comprising a target nucleic acid sequence comprising at least a first target domain and a second target domain, and a first and second ligation probe. The ligation probes may comprise a stuffer sequence of variable length and/or sequence. The first ligation probe comprises a first probe domain substantially complementary to the first target domain, and a 5'-ligation moiety. The second ligation probe comprises a second probe domain substantially complementary to the second target domain, and a 3' ligation moiety. Optionally, the first target domain and the second target domain are separated by at least one nucleotide. Optionally, at least one of the first and said second ligation probes comprises an anchor sequence and/or a label, including a label probe binding sequence. The first and second ligation probes are ligated in the absence of exogenously added ligase enzyme to form a ligation product. The ligated product may optionally be captured on a substrate comprising a capture probe substantially complementary to said anchor sequence and detected. The ligation product may be amplified and detected by capillary electrophoresis, microarray analysis, or any other suitable method.

DETAILED DESCRIPTION OF THE INVENTION

Figure 1:
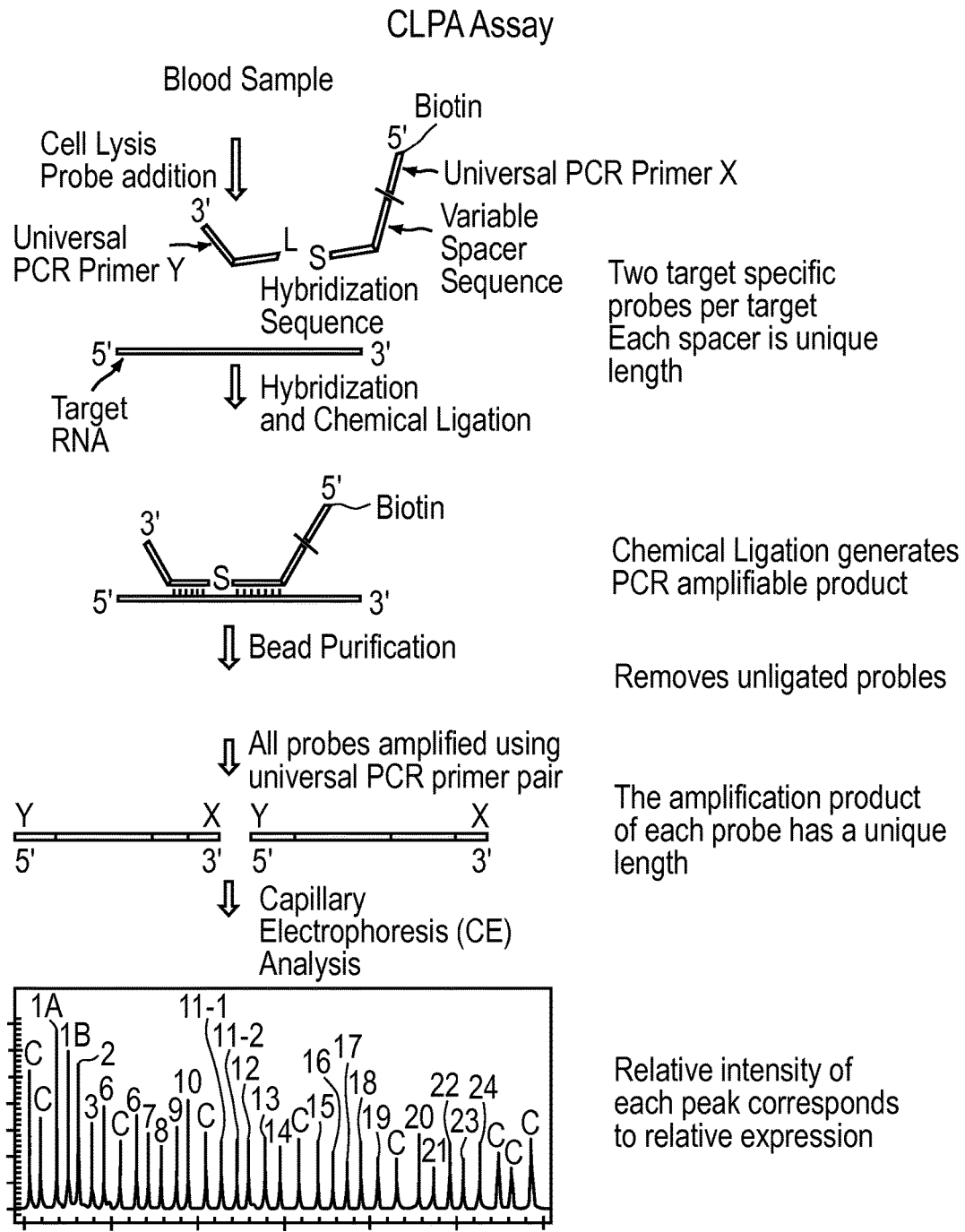
FIG. 1. Schematic representation of one embodiment of CLPA-CE assay.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are hereby incorporated in their entirety by reference for all purposes. Furthermore, all references cited in this application are herein incorporated in their entirety by reference for all purposes.

Overview

The invention provides compositions, apparatus and methods for the detection of one or more nucleic acid targets in a sample including DNA and RNA targets. Moreover, the sample need not be purified. Indeed, one aspect of the invention relates to analyzing impure samples including body samples such as, but not limited to, whole blood. The invention provides methods utilizing two or more oligonucleotide probes that reversibly bind a target nucleic acid in close proximity to each other and possess complementary reactive ligation moieties (it should be noted, as is further described herein, that the reactive moieties are referred to herein as "ligation moieties"). When the probes have bound the target in the proper orientation, they are able to undergo a spontaneous chemical ligation reaction that yields a ligated oligonucleotide product. Following ligation, a new product is generated that can be amplified by an enzymatic or chemical reaction. In the preferred embodiment, the chemical ligation reaction joins two probes that have PCR primer sites on them, e.g. universal PCR primers. Additionally, in one embodiment of the invention, one or both ligation probes contain a stuffer sequence, or variable spacer sequence, which is designed to have differing lengths for each probe set (i.e. each target sequence) thereby resulting in a ligation product having a target-specific length. Following ligation a defined length oligonucleotide can now be exponentially amplified by PCR. In accordance with one aspect of the invention, the probes can possess detectable labels (fluorescent labels, electrochemical labels, magnetic beads, nanoparticles, biotin) to aid in the identification, purification, quantification or detection of the ligated oligonucleotide product. The probes may also optionally include in their structure: anchoring oligonucleotide sequences designed for subsequent capture on a solid support (microarrays, microbeads, nanoparticles), molecule handles that promote the concentration or manipulation of the ligated product (magnetic particles, oligonucleotide coding sequences), and promoter sequences to facilitate subsequent secondary amplification of the ligated product via an enzyme like a DNA or RNA polymerase. The ligation reactions of the invention proceed rapidly, are specific for the target(s) of interest, and can produce multiple copies of the ligated product for each target(s), resulting in an amplification (sometimes referred to herein as "product turnover") of the detectable signal. The ligation reactions of the invention do not require the presence of exogenously added ligases, nor additional enzymes, although some secondary reactions may rely on the use of enzymes such as polymerases, as described below. Ligation chemistries can be chosen from many of the previously described chemical moieties. Preferred chemistries are ones that can be easily incorporated into routine manufacture techniques, are stable during storage, and demonstrate a large preference for target specific ligation when incorporated into a properly designed ligation probe set. Additionally, for embodiments which involve subsequent amplification by an enzyme, ligation chemistries and probe designs (including unnatural nucleotide analogs) that result in a ligation product that can be efficiently processed by an enzyme are preferred. Amplification of the target may also include turnover of the ligation product, in which the ligation product has a lower or comparable affinity for the template or target nucleic acid than do the separate ligation probes. Thus, upon ligation of the hybridized probes, the ligation product is released from the target, freeing the target to serve as a template for a new ligation reaction.

In one embodiment, the ligation reactions of the invention include transfer reactions. In this embodiment, the probes hybridize to the target sequence, but rather than oligonucleotide probes being ligated together to form a ligation product, a nucleic acid-directed transfer of a molecular entity (including reporter molecules such as fluorophores, quenchers, etc) from one oligonucleotide probe to other occurs. This transfer reaction is analogous to a ligation reaction, however instead of joining of two or more probes, one of the probes is ligated to the transfer molecule and the other probe is the "leaving group" of the chemical reaction. We use the term "transfer" reaction so as to distinguish between the different nature of the resulting final product. Importantly, similar to the ligation reaction, the transfer reaction is facilitated by the proximal binding of the transfer probes onto a nucleic acid target, such that significant signal is detected only if the probes have hybridized to the target nucleic acid in close enough proximity to one another (e.g., at adjacent sites) for the transfer reaction to take place.

Samples

Accordingly, in one aspect the present invention provides compositions and methods for detecting the presence or absence of target sequences in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Some embodiments utilize siRNA and microRNA as target sequences (Zhang et al., *J Cell Physiol.* (2007) 210(2):279-89; Osada et al., *Carcinogenesis.* (2007) 28(1):2-12; and Mattes et al., *Am J Respir Cell Mol Biol.* (2007) 36(1):8-12, each of which is incorporated herein by reference in its entirety).

Some embodiments of the invention utilize nucleic acid samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage. Such samples are often not useful for traditional methods of nucleic acid detection, because such studies require a high integrity of the nucleic acid sample so that an accurate measure of nucleic acid expression can be made. Often, gene expression studies in paraffin-embedded samples are limited to qualitative monitoring by using immunohistochemical staining to monitor protein expression levels.

Methods and compositions of the present invention are useful in detection of nucleic acids from paraffin-embedded samples, because the process of fixing and embedding in paraffin often results in degradation of the samples' nucleic acids. The present invention is able to amplify and detect even degraded samples, such as those found in paraffin-embedded samples.

A number of techniques exist for the purification of nucleic acids from fixed paraffin-embedded samples as described in WO 2007/133703 the entire contents of which is herein incorporated by reference.

In a preferred embodiment, the target analytes are nucleic acids. By "nucleic acid" or "oligonucleotide" or grammatical equivalents herein means at least two nucleotides covalently linked together. A nucleic acid of the present invention will generally contain phosphodiester bonds (for example in the case of the target sequences), although in some cases, as outlined below, nucleic acid analogs are included that may have alternate backbones (particularly for use with the ligation probes), comprising, for example, phosphoramide (Beaucage et al., *Tetrahedron* (1993) 49(10):1925 and references therein; Letsinger, *J. Org. Chem.* (1970) 35:3800; Sprinzl et al., *Eur. J. Biochem.* (1977) 81:579; Letsinger et al., *Nucl. Acids Res.* (1986) 14:3487; Sawai et al, *Chem. Lett.* (1984) 805; Letsinger et al., *J. Am. Chem. Soc.* (1988) 110:4470; and Pauwels et al., *Chemica Scripta* (1986) 26:141), phosphorothioate (Mag et al., *Nucleic Acids Res.* (1991) 19:1437; and U.S. Pat. No. 5,644,048), phosphorodithioate (Briu et al., *J. Am. Chem. Soc.* (1989) 111:2321, O-methylphophoroamidite linkages (see Eckstein, *Oligonucleotides and Analogues: A Practical Approach,* Oxford University Press), and peptide nucleic acid backbones and linkages (see Egholm, *J. Am. Chem. Soc.* (1992)114:1895; Meier et al., *Chem. Int. Ed. Engl.* (1992) 31:1008; Nielsen, *Nature,* (1993) 365:566; Carlsson et al., *Nature* (1996) 380:207, all of which are incorporated herein by reference in their entirety). Other analog nucleic acids include those with bicyclic structures including locked nucleic acids, Koshkin et al., *J. Am. Chem. Soc.* (1998) 120:13252 3); positive backbones (Denpcy et al., *Proc. Natl. Acad. Sci. USA* (1995) 92:6097; non-ionic backbones (U.S. Pat. Nos. 5,386,023, 5,637,684, 5,602,240, 5,216,141 and 4,469,863; Kiedrowshi et al., *Angew. Chem. Intl. Ed. English* (1991) 30:423; Letsinger et al., *J. Am. Chem. Soc.* (1988) 110:4470; Letsinger et al., *Nucleoside & Nucleotide* (1994) 13:1597; Chapters 2 and 3, *ASC Symposium Series* 580, Ed. Y. S. Sanghui and P. Dan Cook; Mesmaeker et al., *Bioorganic & Medicinal Chem. Lett.* (1994) 4:395; Jeffs et al., *J. Biomolecular NMR* (1994) 34:17; Xu et al., *Tetrahedron Lett.* (1996) 37:743) and non-ribose backbones, including those described in U.S. Pat. Nos. 5,235,033 and 5,034,506, and Chapters 6 and 7, *ASC Symposium Series* 580, Ed. Y. S. Sanghui and P. Dan Cook. Nucleic acids containing one or more carbocyclic sugars are also included within the definition of nucleic acids (see Jenkins et al., *Chem. Soc. Rev.* (1995) pp 169-176). Several nucleic acid analogs are described in Rawls, *C & E News* Jun. 2, 1997 page 35. All of these references are herein expressly incorporated by reference. These modifications of the ribose-phosphate backbone may be done to facilitate the addition of labels or other moieties, to increase or decrease the stability and half-life of such molecules in physiological environments, etc.

As will be appreciated by those in the art, all of these nucleic acid analogs may find use in the present invention. In addition, mixtures of naturally occurring nucleic acids and analogs can be made; for example, at the site of a ligation moiety, an analog structure may be used. Alternatively, mixtures of different nucleic acid analogs, and mixtures of naturally occurring nucleic acids and analogs may be made.

Nucleic acid analogue may include, for example, peptide nucleic acid (PNA, WO 92/20702, incorporated herein by reference in its entirety) and Locked Nucleic Acid (LNA, Koshkin A A et al. *Tetrahedron* (1998) 54:3607-3630., Koshkin A A et al. *J. Am. Chem. Soc.* (1998) 120:13252-13253., Wahlestedt C et al. *PNAS* (2000) 97:5633-5638, each of which is incorporated herein by reference in its entirety). In some applications analogue backbones of this type may exhibit improved hybridization kinetics, improved thermal stability and improved sensitivity to mismatch sequences.

The nucleic acids may be single stranded or double stranded, as specified, or contain portions of both double stranded or single stranded sequences. The nucleic acid may be DNA, both genomic and cDNA, RNA or a hybrid, where the nucleic acid contains any combination of deoxyribo- and ribo-nucleotides, and any combination of bases, including naturally occurring nucleobases (uracil, adenine, thymine, cytosine, guanine) and non-naturally occurring nucleobases (inosine, xathanine hypoxathanine, isocytosine, isoguanine, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deazaguanine), N9-(7-deaza-8-aza-guanine) and N8-(7-deaza-8-aza-adenine). 5-propynyl-uracil, 2-thio-5-propynyl-uracil) etc. As used herein, the term "nucleobase" includes both "nucleosides" and "nucleotides", and monomers of nucleic acid analogs. Thus, for example, the individual units of a peptide nucleic acid, each containing a base, are referred to herein as a nucleobase.

In one aspect, ligation probes of the invention are any polymeric species that is capable of interacting with a nucleic acid target(s) in a sequence specific manner and possess chemical moieties allowing the probes to undergo a spontaneous chemical ligation reaction with another polymeric species possessing complementary chemical moieties. In one embodiment, the oligonucleotide probes can be DNA, RNA, PNA, LNA, modified versions of the aforementioned and/or any hybrids of the same (e.g. DNA/RNA hybrids, DNA/LNA hybrids, DNA/PNA hybrids). In a preferred embodiment, the oligonucleotide probes are DNA or RNA oligonucleotides.

Nucleic acid samples (e.g. target sequences) that do not exist in a single-stranded state in the region of the target sequence(s) are generally rendered single-stranded in such region(s) prior to detection or hybridization. Generally, nucleic acid samples can be rendered single-stranded in the region of the target sequence using heat denaturation. For polynucleotides obtained via amplification, methods suitable for generating single-stranded amplification products are preferred. Non-limiting examples of amplification processes suitable for generating single-stranded amplification product polynucleotides include, but are not limited to, T7 RNA polymerase run-off transcription, RCA, Asymmetric PCR (Bachmann et al., *Nucleic Acid Res.* (1990) 18:1309), and Asynchronous PCR (WO 01/94638). Commonly known methods for rendering regions of double-stranded polynucleotides single stranded, such as the use of PNA openers (U.S. Pat. No. 6,265,166), may also be used to generate single-stranded target sequences on a polynucleotide.

In one aspect, the invention provides methods of detecting target sequences. By "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA, MicroRNA and rRNA, or others. As is outlined herein, the target sequence may be a target sequence from a sample, or a secondary target such as a product of an amplification reaction, etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

In some embodiments, the target sequence is comprised of different types of target domain. For example, a first target domain of the sample target sequence may hybridize to a first ligation probe, and a second target domain in the target sequence may hybridize to a second ligation probe. Other target domains may hybridize to a capture probe on a substrate such as an array, or a label probe, etc.

The target domains may be adjacent or separated as indicated, as is more fully described below. In some cases, when detection is based on ligation and the application requires amplification of signal, the ligation probes may utilize linkers and be separated by one or more nucleobases of the target sequence to confer hybridization instability on the ligated product. In other applications, for example in single nucleotide polymorphism (SNP) detection, or in transfer reactions, the ligation probes may hybridize to adjacent nucleobases of the target sequence. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. For ease of reference and not to be limiting, these domains are sometimes referred to as "upstream" and "downstream", with the normal convention being the target sequence being displayed in a 5' to 3' orientation The probes are designed such that when the probes bind to a part of the target polynucleotide in close spatial proximity, a chemical ligation reaction occurs between the probes. In general, the probes comprise chemically reactive moieties (herein generally referred to as "ligation moieties") and bind to the target polynucleotide in a particular orientation, such that the chemically reactive moieties come into close spatial proximity, thus resulting in a spontaneous ligation reaction.

Probe Components

In one embodiment, the invention provides sets of ligation probes, usually a first and a second ligation probe, although as is described herein some embodiments utilize more than two. In addition, as noted herein, in some cases a transfer reaction is done rather than ligation; "ligation probes" includes "transfer probes". Each ligation probe comprises a nucleic acid portion, sometimes referred to herein as a "probe domain" that is substantially complementary to one of the target domains. Probes of the present invention are designed to be complementary to a target sequence such that hybridization of the target sequence and the probes of the present invention occurs. As outlined herein, this complementarity need not be perfect; there may be any number of base pair mismatches which will interfere with hybridization between the target sequence and the probes of the present invention. However, if the number of mutations is so great that no hybridization can occur under even the least stringent of hybridization conditions, the sequence is not a complementary sequence. Thus, by "substantially complementary" herein is meant that the probes are sufficiently complementary to the target sequences to hybridize under normal reaction conditions. "Identical" sequences are those that over the length of the shorter sequence of nucleobases, perfect complementarity exists.

In one aspect of the invention, the length of the probe is designed to vary with the length of the target sequence, the specificity required, the reaction (e.g. ligation or transfer) and the hybridization and wash conditions. Generally, in this aspect ligation probes range from about 5 to about 150 nucleobases, with from about 15 to about 100 being preferred and from about 25 to about 75 being especially preferred. In general, these lengths apply equally to ligation and transfer probes.

In another embodiment of the invention, referred to herein as "CLPA-CE" which is described more fully below, probe length is designed to vary for each target of interest thereby generating ligation products that can be identified and analyzed based on length variance.

A variety of hybridization conditions may be used in the present invention, including high, moderate and low stringency conditions; see for example Maniatis et al., *Molecular Cloning: A Laboratory Manual*, 2d Edition, 1989, and Ausubel, et al, *Short Protocols in Molecular Biology*, herein incorporated by reference. The hybridization conditions may also vary when a non-ionic backbone, e.g. PNA is used, as is known in the art.

Ligation Moieties

In addition to ligation domains, the ligation probes of the invention have ligation moieties. Accordingly, in one aspect, the invention relates to methods of chemical ligation that include the binding of at least a first and a second ligation probe to the target nucleic acid to form a "ligation substrate" under conditions such that the ligation moieties of the first and second ligation probes are able to spontaneously react, ligating the probes together, in the absence of exogenous ligase; that is, no exogenous ligase is added to the reaction. In the case of the transfer reaction, this may be referred to as either a "ligation substrate" or a "transfer substrate". By "ligation substrate" herein is meant a substrate for chemical ligation comprising at least one target nucleic acid sequence and two or more ligation probes. Similarly, included within the definition of "ligation substrate" is a "transfer substrate", comprising at least one target nucleic acid sequence and two or more transfer probes.

In some embodiments of the invention, for example when additional specificity is desired, more than two ligation probes can be used. In this embodiment, the "middle" ligation probe(s) can also be adjacent or separated by one or more nucleobases of the target sequence. In a preferred embodiment, the ligation reaction does not require the presence of a ligase enzyme and occurs spontaneously between the bound probes in the absence of any addition (e.g. exogeneous) ligase.

Oligonucleotide probes of the invention are designed to be specific for the polynucleotide target. These probes bind to the target in close spatial proximity to each other and are oriented in such a manner that the chemically reactive moieties are in close spatial proximity. In one aspect, two or more probes are designed to bind near adjacent sites on a target polynucleotide. In a preferred embodiment, two probes bind to the target such that the ligation moiety at the 5' end of one oligonucleotide probe is able to interact with the ligation moiety at the 3' end of the other probe.

Chemical ligation can, under appropriate conditions, occur spontaneously without the addition of any additional activating reagents or stimuli. Alternatively, "activating" agents or external stimuli can be used to promote the chemical ligation reaction. Examples of activating agents include, without limitation, carbodiimide, cyanogen bromide (BrCN), imidazole, 1-methylimidazole/carbodiimide/ cystamine, N-cyanoimidazole, dithiothreitol (DTT), tris(2-carboxyethyl)phosphine (TCEP) and other reducing agents as well as external stimuli like ultraviolet light, heat and/or pressure changes.

As is outlined herein, the ligation moieties of the invention may take a variety of configurations, depending on a number of factors. Most of the chemistries depicted herein are used in phosphoramidite reactions that generally progress in a 3' to 5' direction. That is, the resin contains chemistry allowing attachment of phosphoramidites at the 5' end of the molecule. However, as is known in the art, phosphoramidites can be used to progress in the 5' to 3' direction; thus, the invention includes moieties with opposite orientation to those outlined herein.

Each set of ligation probes (or transfer probes) contains a set of a first ligation moiety and a second ligation moiety. The identification of these ligation moiety pairs depends on the chemistry of the ligation to be used. In addition, as described herein, linkers (including but not limited to destabilization linkers) may be present between the probe domain and the ligation moiety of one or both ligation probes. In general, for ease of discussion, the description herein may use the terms "upstream" and "downstream" ligation probes, although this is not meant to be limiting.

Halo Leaving Group Chemistry

In one embodiment of the invention, the chemistry is based on 5' halogen leaving group technology such as is generally described in Gryanov, S. M., and Letsinger, R. L., (1993) *Nucleic Acids Research*, 21:1403; Xu, Y. and Kool, E. T. (1997) *Tetrahedron Letters*, 38:5595; Xu, Y. and Kool, E. T., (1999) *Nucleic Acids Research*, 27:875; Arar et al., (1995), *BioConj. Chem.*, 6:573; Kool, E. T. et. al, (2001) *Nature Biotechnol* 19:148; Kool, E. T. et. al., (1995) *Nucleic Acids Res*, 23 (17):3547; Letsinger et al., U.S. Pat. No. 5,476,930; Shouten et al., U.S. Pat. No. 6,955,901; Andersen et al., U.S. Pat. No. 7,153,658, all of which are expressly incorporated by reference herein. In this embodiment, the first ligation probe includes at its 5' end a nucleoside having a 5' leaving group, and the second ligation probe includes at its 3' end a nucleoside having 3' nucleophilic group such as a 3' thiophosphoryl. The 5' leaving group can include many common leaving groups know to those skilled in the art including, for example the halo-species (I, Br, Cl) and groups such as those described by Abe and Kool, *J. Am. Chem. Soc.* (2004) 126:13980-13986, which is incorporated herein by reference in its entirety. In a more preferred embodiment of this aspect of the invention, the first ligation probe has a 5' leaving group attached through a flexible linker and a downstream oligonucleotide which has a 3' thiophosphoryl group. This configuration leads to a significant increase in the rate of reaction and results in multiple copies of ligated product being produced for every target.

The "upstream" oligonucleotide, defined in relation to the 5' to 3' direction of the polynucleotide template as the oligonucleotide that binds on the "upstream" side (i.e., the left, or 5' side) of the template includes, as its 5' end, a 5'-leaving group. Any leaving group capable of participating in an $S_N2$ reaction involving sulfur, selenium, or tellurium as the nucleophile can be utilized. The leaving group is an atom or group attached to carbon such that on nucleophilic attack of the carbon atom by the nucleophile (sulfur, selenium or tellurium) of the modified phosphoryl group, the leaving group leaves as an anion. Suitable leaving groups include, but are not limited to a halide, such as iodide, bromide or chloride, a tosylate, benzenesulfonate or p-nitrophenylester, as well as $RSO_3$ where R is phenyl or phenyl substituted with one to five atoms or groups comprising F, Cl, Br, I, alkyl (C1 to C6), nitro, cyano, sulfonyl and carbonyl, or R is alkyl with one to six carbons. The leaving group is preferably an iodide, and the nucleoside at the 5' end of the upstream oligonucleotide is, in the case of DNA, a 5'-deoxy-5'-iodo-2'-deoxynucleoside. Examples of suitable 5'-deoxy-5'-iodo-2'-deoxynucleosides include, but are not limited to, 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof (see FIG. 2). In the case of RNA oligonucleotides, analogous examples of suitable 5'-deoxy-5'-iodonucleosides include, but are not limited to, 5'-deoxy-5'-iodouracil (5'-I-U), 5'-deoxy-5'-iodocytidine (5'-I-C), 5'-deoxy-5'-iodoadenosine (5'-I-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof. In a preferred embodiment, an upstream ligation probe contains 2'-deoxyribonucleotides except that the modified nucleotide on the 5' end, which comprises the 5' leaving group, is a ribonucleotide. This embodiment of the upstream nucleotide is advantageous because the bond between the penultimate 2'-deoxyribonucleotide and the terminal 5' ribonucleotide is susceptible to cleavage using base. This allows for potential reuse of an oligonucleotide probe that is, for example, bound to a solid support, as described in more detail below. In reference to the CLPA assay, which is described more fully below, the 5' leaving group of the "upstream" probe is most preferably DABSYL.

The "downstream" oligonucleotide, which binds to the polynucleotide template "downstream" of, i.e., 3' to, the upstream oligonucleotide, includes, as its 3' end, a nucleoside having linked to its 3' hydroxyl a phosphorothioate group (i.e., a "3'-phosphorothioate group"), a phosphoroselenoate group (i.e., a "3'-phosphoroselenoate group), or a phosphorotelluroate group (i.e., a "3'-phosphorotelluroate group"). The chemistries used for autoligation are thus sulfur-mediated, selenium-mediated, or tellurium mediated. Self-ligation yields a ligation product containing a 5' bridging phosphorothioester (—O—P(O)(O.sup.-)-S—), phosphoroselenoester (—O—P(O)(O.sup.-)-Se—) or phosphorotelluroester (—O—P(O)(O.sup.-)-Te—), as dictated by the group comprising the 3' end of the downstream oligonucleotide. This non-natural, achiral bridging diester is positioned between two adjacent nucleotides and takes the place of a naturally occurring 5' bridging phosphodiester. Surprisingly, the selenium-mediated ligation is 3 to 4 times faster than the sulfur-mediated ligation, and the selenium-containing ligation product was very stable, despite the lower bond strength of the Se—P bond. Further, the bridging phosphoroselenoester, as well as the bridging phosphorotelluroester, are expected to be cleavable selectively by silver or mercuric ions under very mild conditions (see Mag et al., *Nucleic Acids Res.* (1991) 19:1437 1441).

In one embodiment, a downstream oligonucleotide contains 2'-deoxyribonucleotides except that the modified nucleotide on the 3' end, which comprises the 3' phosphorothioate, phosphoroselenoate, or phosphorotelluroate, is a ribonucleotide. This embodiment of the upstream nucleotide is advantageous because the bond between the penultimate 2'-deoxyribonucleotide and the terminal ribonucleotide is susceptible to cleavage using base, allowing for potential reuse of an oligonucleotide probe that is, for example, bound to a solid support. In reference to the CLPA assay, as described more fully below, the "downstream" probe most preferably includes at its 3' end 3'-phosphorothioate.

It should be noted that the "upstream" and "downstream" oligonucleotides can, optionally, constitute the two ends of a single oligonucleotide, in which event ligation yields a circular ligation product. The binding regions on the 5' and 3' ends of the linear precursor oligonucleotide must be linked by a number of intervening nucleotides sufficient to allow binding of the 5' and 3' binding regions to the polynucleotide target.

Compositions provided by the invention include a 5'-deoxy-5'-'iodo-2'-deoxynucleoside, for example a 5'-deoxy-5'-iodothymidine (5'-I-T), 5'-deoxy-5'-iodo-2'-deoxycytidine (5'-I-dC), 5'-deoxy-5'-iodo-2'-deoxyadenosine (5'-I-dA), 5'-deoxy-5'-iodo-3-deaza-2'-deoxyadenosine (5'-I-3-deaza-dA), 5'-deoxy-5'-iodo-2'-deoxyguanosine (5'-I-dG) and 5'-deoxy-5'-iodo-3-deaza-2'-deoxyguanosine (5'-I-3-deaza-dG), and the phosphoroamidite derivatives thereof, as well as an oligonucleotide comprising, as its 5' end, a 5'-deoxy-5'-iodo-2'-deoxynucleoside of the invention. Compositions provided by the invention further include a 5'-deoxy-5'-iodonucleoside such as 5'-deoxy-5'-iodouracil (5'-I-U), 5'-deoxy-5'-iodocytidine (5'-I-C), 5'-deoxy-5'-iodoadenosine (5'-1-A), 5'-deoxy-5'-iodo-3-deazaadenosine (5'-I-3-deaza-A), 5'-deoxy-5'-iodoguanosine (5'-I-G) and 5'-deoxy-5'-iodo-3-deazaguanosine (5'-I-3-deaza-G), and the phosphoroamidite derivatives thereof, as well as an oligonucleotide comprising, as its 5' end, a 5'-deoxy-5'-iodonucleoside of the invention. Also included in the invention is a nucleoside comprising a 3'-phosphoroselenoate group or a 3'-phosphorotelluroate group, and an oligonucleotide comprising as its 3' end a nucleoside comprising a 3'-phosphoroselenoate group or a 3'-phosphorotelluroate group. Oligonucleotides containing either or both of these classes of modified nucleosides are also included in the invention, as are methods of making the various nucleosides and oligonucleotides. Oligonucleotides that are modified at either or both of the 5' or 3' ends in accordance with the invention optionally, but need not, include a detectable label, preferably a radiolabel, a fluorescence energy donor or acceptor group, an excimer label, or any combination thereof.

In addition, in some cases, substituent groups may also be protecting groups (sometimes referred to herein as "PG"). Suitable protecting groups will depend on the atom to be protected and the conditions to which the moiety will be exposed. A wide variety of protecting groups are known; for example, DMT is frequently used as a protecting group in phosphoramidite chemistry (as depicted in the figures; however, DMT may be replaced by other protecting groups in these embodiments. A wide variety of protecting groups are suitable; see for example, Greene's Protective Groups in Organic Synthesis, herein incorporated by reference for protecting groups and associated chemistry.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant $NH_2$, —NHR and —$NR_2$ groups, with R being as defined herein. In some embodiments, for example in the case of the peptide ligation reactions, primary and secondary amines find particular use, with primary amines generally showing faster reaction rates.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). A particular type of sulfur containing moiety is a thioester (—(CO)—S—), usually found as a substituted thioester (—(CO)—SR). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCOH groups.

By "alcohol" herein is meant —OH groups, and alkyl alcohols —ROH.

By "amido" herein is meant —RCONH— or RCONR— groups.

By "ethylene glycol" herein is meant a —(O—$CH_2$—$CH_2)_n$— group, although each carbon atom of the ethylene group may also be singly or doubly substituted, i.e. —(O—$CR_2$—$CR_2)_n$—, with R as described above. Ethylene glycol derivatives with other heteroatoms in place of oxygen (i.e. —(N—$CH_2$—$CH_2)_n$— or —(S—$CH_2$—$CH_2)_n$—, or with substitution groups) are also preferred.

Additionally, in some embodiments, the R group may be a functional group, including quenchers, destabilization moieties and fluorophores (as defined below). Fluorophores of particular use in this embodiment include, but are not limited to Fluorescein and its derivatizes, TAMRA (Tetramethyl-6-carboxyrhodamine), Alexa dyes, and Cyanine dyes (e.g. Cy3 and Cy5).

Quencher moieties or molecules are known in the art, and are generally aromatic, multiring compounds that can deactivate the excited state of another molecule. Fluorophore-quencher pairs are well known in the art. Suitable quencher moieties include, but are not limited to Dabsyl (Dimethylamini(azobenzene)sulfonyl) Dabcyl (Dimethylamino (azobenzene)carbonyl), Eclipse Quenchers (Glen Research Catalog) and blackhole Quenchers (BHQ-1, BHQ-2 and BHQ-3) from Biosearch Technologies.

Suitable destabilization moieties are discussed below and include, but are not limited to molecule entities that result in a decrease in the overall binding energy of an oligonucleotide to its target site. Potential examples include, but are not limited to alkyl chains, charged complexes, and ring structures.

Nucleophile Ligation Moieties

In this embodiment, the other ligation probe comprises a ligation moiety comprising a nucleophile such as an amine. Ligation moieties comprising both a thiol and an amine find particular use in certain reactions. In general, the nucleophile ligation moieties can include a wide variety of potential amino, thiol compounds as long as the nucleophile ligation moiety contains a thiol group that is proximal to a primary or secondary amino and the relative positioning is such that at least a 5 or 6 member ring transition state can be achieve during the S to N acyl shift.

Accordingly, nucleophile ligation molecules that comprise 1, 2 or 1, 3 amine thiol groups find particular use. Primary amines find use in some embodiments when reaction time is important, as the reaction time is generally faster for primary than secondary amines, although secondary amines find use in acyl transferase reactions that contribute to destabilization as discussed below. The carbons between the amino and thiol groups can be substituted with non-hydrogen R groups, although generally only one non-hydrogen R group per carbon is utilized. Additionally, adjacent R groups (depicted as R' and R" in Figure *CC) may be joined together to form cyclic structures, including substituted and unsubstituted cycloalkyl and aryl groups, including heterocycloalkyl and heteroaryl and the substituted and unsubstituted derivatives thereof. In the case where a 1,2 amino thiol group is used and adjacent R groups are attached, it is generally preferred that the adjacent R groups form cycloalkyl groups (including heterocycloalkyl and substituted derivatives thereof) rather than aryl groups.

In this embodiment, for the generation of the 4 sigma bond contraction of the chain for destabilization, the replacement ligation moiety relies on an acyl transferase reaction.

Linkers

In many embodiments, linkers (sometimes shown herein as "L" or "-(linker)$_n$-"), (where n is zero or one) may optionally be included at a variety of positions within the ligation probe(s). Suitable linkers include alkyl and aryl groups, including heteroalkyl and heteroaryl, and substituted derivatives of these. In some instances, for example when Native Peptide Ligation reactions are done, the linkers may be amino acid based and/or contain amide linkages. As described herein, some linkers allow the ligation probes to be separated by one or more nucleobases, forming abasic sites within the ligation product, which serve as destabilization moieties, as described below.

Destabilization Moieties

In accordance with one aspect of the invention, it is desirable to produce multiple copies of ligated product for each target molecule without the aid of an enzyme. One way to achieve this goal involves the ligated product disassociating from the target following the chemical ligation reaction to allow a new probe set to bind to the target. To increase ligation product turnover, probe designs, instrumentation, and chemical ligation reaction chemistries that increase product disassociation from the target molecule are desirable.

Previous work has shown one way to achieve product disassociation and increase product turnover is to "heat cycle" the reaction mixture. Heat cycling is the process of varying the temperature of a reaction so as to facilitate a desired outcome. Most often heat cycling takes the form of briefly raising the temperature of the reaction mixture so that the reaction temperature is above the melting temperature of the ligated product for a brief period of time causing the product to disassociate from the target. Upon cooling, a new set of probes is able to bind the target, and undergo another ligation reaction. This heat cycling procedure has been practiced extensively for enzymatic reactions like PCR.

While heat cycling is one way to achieve product turnover, it is possible to design probes such that there is significant product turnover without heat cycling. Probe designs and ligation chemistries that help to lower the melting temperature of the ligated product increase product turnover by decreasing product inhibition of the reaction cycle.

Accordingly, in one aspect, the probes are designed to include elements (e.g. destabilization moieties), which, upon ligation of the probes, serve to destabilize the hybridization of the ligation product to the target sequence. As a result, the ligated substrate disassociates after ligation, resulting in a turnover of the ligation product, e.g. the ligation product comprising the two ligation probes dehybridizes from the target sequence, freeing the target sequence for hybridization to another probe set.

In addition, increasing the concentration of the free (e.g. unhybridized) ligation probes can also help drive the equilibrium towards release of the ligation product (or transfer product) from the target sequence. Accordingly, some embodiments of the invention use concentrations of probes that are 1,000,000 fold higher than that of the target while in other embodiments the probes are 10,000 to 100 fold higher than that of the target. As will be appreciated by those skilled in the art, increasing the concentration of free probes can be used by itself or with any embodiment outlined herein to achieve product turnover (e.g. amplification). While increasing the probe concentration can result in increased product turnover, it can also lead to significant off target reactions such as probe hydrolysis and non-target mediated ligation.

In one aspect, probe elements include structures which lower the melting temperature of the ligated product. In some embodiments, probe elements are designed to hybridize to non-adjacent target nucleobases, e.g. there is a "gap" between the two hybridized but unligated probes. In general, this is done by using one or two linkers between the probe domain and the ligation moiety. That is, there may be a linker between the first probe domain and the first ligation moiety, one between the second probe domain and the second ligation moiety, or both. In some embodiments, the gap comprises a single nucleobase, although more can also be utilized as desired. As will be appreciated by those skilled in the art, there may be a tradeoff between reaction kinetics and length of the linkers; if the length of the linker(s) are so long that contact resulting in ligation is kinetically disfavored, shorter linkers may be desired. However, in some cases, when kinetics are not important, the length of the gap and the resulting linkers may be longer, to allow spanning gaps of 1 to 10 nucleobases. Generally, in this embodiment, what is important is that the length of the linker(s) roughly corresponds to the number of nucleobases in the gap.

In another aspect of this embodiment of the invention, the formation of abasic sites in a ligation product as compared to the target sequence serves to destabilize the duplex. For example, Abe and Kool (J. Am. Chem. Soc. (2004) 126: 13980-13986) compared the turnover when two different 8-mer oligonucleotide probes (Bu42 and DT40) were ligated with the same 7-mer probe (Thio 4). When Thio4 is ligated with DT40, a continuous 15-mer oligonucleotide probe with a nearly native DNA structure is formed that should be perfectly matched with the DNA target. However, when Thio4 is ligated with Bu42, a 15-mer oligonucleotide probe is formed, but when the probe is bound to the target, it has an abasic site in the middle that is spanned by an alkane linker. Comparison of the melting temperature (Tm) of these two probes when bound to the target shows approximately a 12° C. difference in melting temperature (58.5 for Bu42 versus 70.7° C. for DT40). This 12° C. difference in melting temperature led to roughly a 10-fold increase in product turnover (91.6-Bu42 versus 8.2 DT40) at 25° C. when the probe sets (10,000-fold excess, 10 µM conc) were present in large excess compared to the target (1 nM). Similarly, Dose et al (Dose 2006) showed how a 4° C. decrease in Tm for two identical sequences, chemically ligated PNA probes (53° C. versus 57° C.) results in approximately a 4-fold increase in product turnover.

Recent work has demonstrated the use of chemical ligation based Quenched Auto-Ligation (QUAL) probes to monitor RNA expression and detect single base mismatches inside bacterial and human cells (WO 2004/0101011 herein incorporated by reference).

In one embodiment, destabilization moieties are based on the removal of stabilization moieties. That is, if a ligation probe contains a moiety that stabilizes its hybridization to the target, upon ligation and release of the stabilization moiety, there is a drop in the stability of the ligation product. Accordingly, one general scheme for reducing product inhibition is to develop probes that release a molecular entity like a minor groove binding molecule during the course of the initial chemical ligation reaction or following a secondary reaction post ligation. Depending on the oligonucleotide sequence, minor groove binders like the dihydropyrroloindole tripeptide ($DPI_3$) described by Kutyavin (Kutyavin 1997 and Kutyavin 2000) can increase the Tm of a duplex nucleic acid by up to 40° C. when conjugated to the end of an oligonucleotide probe. In contrast, the unattached version of the DPI3 only increases the Tm of the same duplex by 2° C. or so. Thus, minor groove binders can be used to produce probe sets with enhanced binding strengths, however if the minor groove binder is released during the course of the reaction, the binding enhancement is loss and the ligated product will display a decreased Tm relative to probes in which the minor groove binder is still attached.

Suitable minor groove binding molecules include, but are not limited to, dihydropyrroloindole tripeptide ($DPI_3$), distamycin A, and pyrrole-imidazole polyamides (Gottesfeld, J. M., et al., *J. Mol. Biol.* (2001) 309:615-629.

In addition to minor groove binding molecules tethered intercalators and related molecules can also significantly increase the melting temperature of oligonucleotide duplexes, and this stabilization is significantly less in the untethered state. (Dogan, et al., *J. Am. Chem Soc.* (2004) 126:4762-4763 and Narayanan, et al., *Nucleic Acids Research,* (2004) 32:2901-2911).

Similarly, as will be appreciated by those in the art, probes with attached oligonucleotide fragments (DNA, PNA, LNA, etc) capable of triple helix formation, can serve as stabilization moieties that upon release, results in a decrease of stabilization of the ligation product to the target sequence (Pooga, M, et al., *Biomolecular Engineering* (2001) 17:183-192.

Another general scheme for decreasing product inhibition by lowering the binding strength of the ligated product is to incorporate abasic sites at the point of ligation. This approach has been previously demonstrated by Abe (*J. Am. Chem. Soc.* (2004) 126:13980-13986), however it is also possible to design secondary probe rearrangements to further amplify the decrease in Tm via straining the alignment between the ligated probes and the target. For example, Dose et al. (*Org. Letters* (2005) 7:20 4365-4368) showed how a rearrangement post-ligation that changed the spacing between PNA bases from the ideal 12 sigma bonds to 13 resulted in a lowering of the Tm by 4° C. Larger rearrangements and secondary reactions that interfere with the binding of the product to the target or result in the loss of oligonucleotide bases can further decrease the Tm.

The present invention provides methods and compositions for a ligation reaction that results in a chain contraction of up to 4 sigma bonds during the rearrangement, which should have a significant effect on the Tm post-rearrangement compared to the 1 base expansion using the chemistry described by Dose. This chemistry is based on the acyl transfer auxiliary that has been described previously (Offer et al., *J Am Chem Soc.* (2002) 124(17):4642-6). Following completion of the chain contraction, a free-thiol is generated that is capable of undergoing another reaction either with a separate molecule or with itself. For example, this thiol could react with an internal thioester to severely kink the oligonucleotide and thus further decrease the ligation product's ability to bind to the target.

Thus, in this embodiment, ligation reactions that release functional groups that will undergo a second reaction with the ligation product can reduce stabilization of the hybrid of the ligation product and the target sequence.

Additional Functionalities of Ligation Probes

In addition to the target domains, ligation moieties, and optional linkers, one or more of the ligation probes of the invention can have additional functionalities, including, but not limited to, promoter and primer sequences (or complements thereof, depending on the assay), labels including label probe binding sequences and anchor sequences. Additional functionalities including variable spacer sequences (also referred to as stuffer sequences) are described hereinbelow with reference to the CLPA assay.

In one aspect of the invention, the upstream oligonucleotide probe can have a promoter site or primer binding site for a subsequent enzymatic amplification reaction. In one embodiment, the upstream probe contains the promoter sequence for a RNA polymerase, e.g. T7, SP6 or T3. In another embodiment, both the upstream and down stream oligonucleotides contain primer binding sequences. Promoter and primer binding sequences are designed so as to not interact with the nucleic acid targets to any appreciable extent. In a preferred embodiment, when detecting multiple targets simultaneously, all of the oligonucleotide probe sets in the reaction are designed to contain identical promoter or primer pair binding sites such that following ligation and purification, if appropriate, all of the ligated products can be amplified simultaneously using the same enzyme and/or same primers.

In one embodiment, one or more of the ligation probes comprise a promoter sequence. In embodiments that employ a promoter sequence, the promoter sequence or its complement will be of sufficient length to permit an appropriate polymerase to interact with it. Detailed descriptions of sequences that are sufficiently long for polymerase interaction can be found in, among other places, Sambrook and Russell. In certain embodiments, amplification methods comprise at least one cycle of amplification, for example, but not limited to, the sequential procedures of: interaction of a polymerase with a promoter; synthesizing a strand of nucleotides in a template-dependent manner using a polymerase; and denaturing the newly-formed nucleic acid duplex to separate the strands.

In another embodiment, one or both of the ligation probes comprise a primer sequence. As outlined below, the ligation products of the present invention may be used in additional reactions such as enzymatic amplification reactions. In one embodiment, the ligation probes include primer sequences designed to allow an additional level of amplification. As used herein, the term "primer" refers to nucleotide sequence, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. One or more of the nucleotides of the primer can be modified, for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the target strand.

By using several priming sequences and primers, a first ligation product can serve as the template for additional ligation products. These primer sequences may serve as priming sites for PCR reactions, which can be used to amplify the ligation products. In addition to PCR reactions, other methods of amplification can utilize the priming sequences, including but not limited to ligase chain reactions, Invader™, positional amplification by nick translation (NICK), primer extension/nick translation, and other methods known in the art. As used herein, "amplification" refers to an increase in the number of copies of a particular nucleic acid. Copies of a particular nucleic acid made in vitro in an amplification reaction are called "amplicons" or "amplification products".

Amplification may also occur through a second ligation reaction, in which the primer sites serve as hybridization sites for a new set of ligation probes which may or may not comprise sequences that are identical to the first set of ligation probes that produced the original ligation products. The target sequence is thus exponentially amplified through amplification of ligation products in subsequent cycles of amplification.

In another embodiment of this aspect of the invention, the primer sequences are used for nested ligation reactions. In such nested ligation reactions, a first ligation reaction is accomplished using methods described herein such that the ligation product can be captured, for example by using biotinylated primers to the desired strand and capture on beads (particularly magnetic beads) coated with streptavidin. After the ligation products are captured, a second ligation reaction is accomplished by hybridization of ligation probes to primer sequences within a section of the ligation product which is spatially removed from (i.e., downstream from) the end of the ligation product which is attached to the capture bead, probe, etc. At least one of the primer sequences for the secondary ligation reaction will be located within the region of the ligation product complementary to the ligation probe which is not the ligation probe that included the anchor or capture sequence. The ligation products from this second ligation reaction will thus necessarily only result from those sequences successfully formed from the first chemical ligation, thus removing any "false positives" from the amplification reaction. In another embodiment, the primer sequences used in the secondary reaction may be primer sites for other types of amplification reactions, such as PCR.

In one embodiment, one or more of the ligation probes comprise an anchor sequence. By "anchor sequence" herein is meant a component of a ligation probe that allows the attachment of a ligation product to a support for the purposes of detection. Suitable means for detection include a support having attached thereto an appropriate capture moiety. Generally, such an attachment will occur via hybridization of the anchor sequence with a capture probe, which is substantially complementary to the anchor sequence.

In one embodiment of this aspect of the invention, the upstream oligonucleotide is designed to have an additional nucleotide segment that does not bind to the target of interest, but is to be used to subsequently capture the ligated product on a suitable solid support or device of some sort. In a preferred embodiment of this aspect of the invention, the downstream oligonucleotide has a detectable label attached to it, such that following ligation, the resulting product will contain a capture sequence for a solid support at its 3' end and a detectable label at its 5' end, and only ligated products will contain both the capture sequence and the label.

In another aspect of the invention pertaining to multiplex target detection, each upstream probe of a probe set may be designed to have a unique sequence at is 3' end that corresponds to a different position on a DNA array. Each downstream probe of a probe set may optionally contain a detectable label that is identical to the other down stream probes, but a unique target binding sequence that corresponds to its respective targets. Following hybridization with the DNA array, only ligated probes that have both an address sequence (upstream probe) and a label (downstream probe) will be observable.

In another aspect of the invention, the detectable label can be attached to the upstream probe and the capture sequence can be a part of the downstream probe, such that the ligated products will have the detectable label more towards the 3' end and the capture sequence towards the 5' end of the ligated product. The exact configuration is best determined via consideration of the ease of synthesis as well as the characteristics of the devices to be used to subsequently detect the ligated reaction product.

The anchor sequence may have both nucleic and non-nucleic acid portions. Thus, for example, flexible linkers such as alkyl groups, including polyethylene glycol linkers, may be used to provide space between the nucleic acid portion of the anchor sequence and the support surface. This may be particularly useful when the ligation products are large.

In addition, in some cases, sets of anchor sequences that correspond to the capture probes of "universal arrays" can be used. As is known in the art, arrays can be made with synthetic generic sequences as capture probes, that are designed to non-complementary to the target sequences of the sample being analyzed but to complementary to the array binding sequences of the ligation probe sets. These "universal arrays" can be used for multiple types of samples and diagnostics tests because same array binding sequences of the probes can be reused/paired with different target recognition sequences.

In one embodiment, one or more of the ligation probes comprise a label. By "label" or "labeled" herein is meant that a compound has at least one element, isotope or chemical compound attached to enable the detection of the compound, e.g. renders a ligation probe or ligation or transfer product detectable using known detection methods, e.g., electronic, spectroscopic, photochemical, or electrochemiluminescent methods. In general, labels fall into three classes: a) isotopic labels, which may be radioactive or heavy isotopes; b) magnetic, electrical, thermal; and c) colored or luminescent dyes; although labels include enzymes and particles such as magnetic particles as well. The dyes may be chromophores or phosphors but are preferably fluorescent dyes, which due to their strong signals provide a good signal-to-noise ratio. Suitable dyes for use in the invention include, but are not limited to, fluorescent lanthanide complexes, including those of Europium and Terbium, fluorescein, fluorescein isothiocyanate, carboxy-fluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), and others described in the 6th Edition of the Molecular Probes Handbook by Richard P. Haugland, herein expressly incorporated by reference. Additional labels include nanocrystals or Q-dots as described in U.S. Ser. No. 09/315,584, herein expressly incorporated by reference.

In a preferred embodiment, the label is a secondary label that part of a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding protein pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents.

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to a ligation probe) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$ to $10^{-6}$ $M^{-1}$, with less than about $10^{-5}$ to $10^{-9}$ $M^{-1}$ being preferred and $10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo-or hetero-bifunctional linkers as are well known (see 1994 Pierce Chemical Company catalog, technical section on cross-linkers, pages 155 200, incorporated herein by reference).

In this embodiment, the label may also be a label probe binding sequence or complement thereof. By "label probe" herein is meant a nucleic acid that is substantially complementary to the binding sequence and is labeled, generally directly.

Synthetic Methods

The compositions of the invention are generally made using known synthetic techniques. In general, methodologies based on standard phosphoramidite chemistries find particular use in one aspect of the present invention, although as is appreciated by those skilled in the art, a wide variety of nucleic acid synthesic reactions are known.

Methods of making probes having halo leaving groups is known in the art; see for example Abe et al., *Proc Natl Acad Sci USA* (2006)103(2):263-8; Silverman et al., *Nucleic Acids Res.* (2005) 33(15):4978-86; Cuppolletti et al., *Bioconjug Chem.* (2005) 16(3):528-34; Sando et al., *J Am Chem Soc.* (2004) 4;126(4):1081-7; Sando et al., *Nucleic Acids Res Suppl.* (2002) 2:121-2; Sando et al., *J Am Chem Soc.* (2002) 124(10):2096-7; Xu et al., *Nat Biotechnol.* (2001) 19(2): 148-52; Xu et al., *Nucleic Acids Res.* (1998) 26(13):3159-64; Moran et al., *Proc Natl Acad Sci USA* (1997) 94(20): 10506-11; Kool, U.S. Pat. No. 7,033,753; Kool, U.S. Pat. No. 6,670,193; Kool, U.S. Pat. No. 6,479,650; Kool, U.S. Pat. No. 6,218,108; Kool, U.S. Pat. No. 6,140,480; Kool, U.S. Pat. No. 6,077,668; Kool, U.S. Pat. No. 5,808,036; Kool, U.S. Pat. No. 5,714,320; Kool, U.S. Pat. No. 5,683, 874; Kool, U.S. Pat. No. 5,674,683; and Kool, U.S. Pat. No. 5,514,546, each of which is incorporated herein by reference in its entirety.

Additional components such as labels, primer sequences, promoter sequences, etc. are generally incorporated as is known in the art. The spacing of the addition of fluorophores and quenchers is well known as well.

Secondary Reactions

Prior to detecting the ligation or transfer reaction product, there may be additional amplification reactions. Secondary amplification reactions can be used to increase the signal for detection of the target sequence; e.g. by increasing the number of ligated products produced per copy of target. In one embodiment, any number of standard amplification reactions can be performed on the ligation product, including, but not limited to, strand displacement amplification (SDA), nucleic acid sequence based amplification (NASBA), ligation amplification and the polymerase chain reaction (PCR); including a number of variations of PCR, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR". "panhandle PCR", and "PCR select cDNA subtraction", among others. In one embodiment, the amplification technique is not PCR. According to certain embodiments, one may use ligation techniques such as gap-filling ligation, including, without limitation, gap-filling OLA and LCR, bridging oligonucleotide ligation, FEN-LCR, and correction ligation. Descriptions of these techniques can be found, among other places, in U.S. Pat. No. 5,185,243, published European Patent Applications EP 320308 and EP 439182, published PCT Patent Application WO 90/01069, published PCT Patent Application WO 02/02823, and U.S. patent application Ser. No. 09/898,323.

In addition to standard enzymatic amplification reactions, it is possible to design probe schemes where the ligated product that is initially produced can itself be the target of a secondary chemical ligation reaction.

Furthermore, "preamplification reactions" can be done on starting sample nucleic acids to generate more target sequences for the chemical reaction ligation. For example, whole genome amplification can be done.

Assays

As will be appreciated by those skilled in the art, assays utilizing methods and compositions of the invention can take on a wide variety of configurations, depending on the desired application, and can include in situ assays (similar to FISH), solution based assays (e.g. transfer/removal of fluorophores and/or quenchers), and heterogeneous assays (e.g. utilizing solid supports for manipulation, removal and/or detection, such as the use of high density arrays). In addition, assays can include additional reactions, such as pre-amplification of target sequences and secondary amplification reactions after ligation has occurred, as is outlined herein.

Assays pertaining to this aspect of the invention, as described herein, may rely on increases in a signal, e.g. the generation of fluorescence or chemiluminescence. However, as will be appreciated by those in the art, assays that rely on decreases in such signals are also possible.

In one embodiment, assay reactions are performed "in situ" (also referred to in various assay formats as "in vitro" and/or "ex vivo" depending on the sample), similar to FISH reactions. Since no exogenous enzymes need be added, reagents can be added to cells (living, electroporated, fixed, etc.) such as histological samples for the determination of the presence of target sequences, particularly those associated with disease states or other pathologies.

In addition, "in vitro" assays can be done where target sequences are extracted from samples. Samples can be processed (e.g. for paraffin embedded samples, the sample can be prepared), the reagents added and the reaction allowed to proceed, with detection following as is done in the art.

In one embodiment, ligated products are detected using solid supports. For example, the ligated products are attached to beads, using either anchor probe/capture probe hybridization or other binding techniques, such as the use of a binding partner pair (e.g. biotin and streptavidin). In one embodiment, a transfer reaction results in a biotin moiety being transferred from the first ligation probe to a second ligation probe comprising a label. Beads comprising streptavidin are contacted with the sample, and the beads are examined for the presence of the label, for example using FACS technologies.

In other embodiments, ligated products are detected using heterogeneous assays. That is, the reaction is done in solution and the product is added to a solid support, such as an array or beads. Generally, one ligation probe comprises an anchor sequence or a binding pair partner (e.g. biotin, haptens, etc.) and the other comprises a label (e.g. a fluorophore, a label probe binding sequence, etc.). The ligated product is added to the solid support, and the support optionally washed. In this embodiment, only the ligated product will be captured and be labeled.

In another aspect of the invention, one of oligonucleotide probes has an attached magnetic bead or some other label (biotin) that allows for easy manipulation of the ligated product. The magnetic bead or label can be attached to either the upstream or the downstream probe using any number of configurations as outlined herein.

As described herein, secondary reactions can also be done, where additional functional moieties (e.g. anchor sequences, primers, labels, etc.) are added. Similarly, secondary amplification reactions can be done as described herein.

Detection systems are known in the art, and include optical assays (including fluorescence and chemiluminescent assays), enzymatic assays, radiolabelling, surface plasmon resonance, magnetoresistance, cantilever deflection, surface plasmon resonance, etc. In some embodiments, the ligated product can be used in additional assay technologies, for example, as described in 2006/0068378, hereby incorporated by reference, the ligated product can serve as a linker between light scattering particles such as colloids, resulting in a color change in the presence of the ligated product.

In some embodiments, the detection system can be included within the sample collection tube; for example, blood collection devices can have assays incorporated into the tubes or device to allow detection of pathogens or diseases.

Solid Supports

As outlined above, the assays can be run in a variety of ways. In assays that utilize detection on solid supports, there are a variety of solid supports, including arrays, that find use in the invention.

In some embodiments, solid supports such as beads find use in the present invention. For example, binding partner pairs (one on the ligated product and one on the bead) can be used as outlined above to remove non-ligated reactants. In this embodiment, magnetic beads are particularly preferred.

In some embodiments of the invention, capture probes are attached to solid supports for detection. For example, capture probes can be attached to beads for subsequent analysis using any suitable technique, e.g. FACS. Similarly, bead arrays as described below may be used.

In one embodiment, the present invention provides arrays, each array location comprising at a minimum a covalently attached nucleic acid probe, generally referred to as a "capture probe". By "array" herein is meant a plurality of nucleic acid probes in an array format; the size of the array will depend on the composition and end use of the array. Arrays containing from about 2 different capture ligands to many thousands can be made. Generally, for electrode-based assays, the array will comprise from two to as many as 100,000 or more, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture probe may be made as well. In addition, in some arrays, multiple substrates may be used, either of different or identical compositions. Thus, for example, large arrays may comprise a plurality of smaller substrates. Nucleic acid arrays are known in the art, and can be classified in a number of ways; both ordered arrays (e.g. the ability to resolve chemistries at discrete sites), and random arrays (e.g. bead arrays) are included. Ordered arrays include, but are not limited to, those made using photolithography techniques (e.g. Affymetrix GeneChip®), spotting techniques (Synteni and others), printing techniques (Hewlett Packard and Rosetta), electrode arrays, three dimensional "gel pad" arrays and liquid arrays.

In a preferred embodiment, the arrays are present on a substrate. By "substrate" or "solid support" or other grammatical equivalents herein is meant any material that can be modified to contain discrete individual sites appropriate for the attachment or association of nucleic acids. The substrate can comprise a wide variety of materials, as will be appreciated by those skilled in the art, including, but not limited to glass, plastics, polymers, metals, metalloids, ceramics, and organics. When the solid support is a bead, a wide variety of substrates are possible, including but not limited to magnetic materials, glass, silicon, dextrans, and plastics.

Hardware

Microfluidics

In another aspect of the invention, a fluidic device similar to those described by Liu (2006) is used to automate the methodology described in this invention. See for example U.S. Pat. No. 6,942,771, herein incorporated by reference for components including but not limited to cartridges, devices, pumps, wells, reaction chambers, and detection chambers. The fluidic device may also include zones for capture of magnetic particles, separation filters and resins, including membranes for cell separation (i.e. Leukotrap™ from Pall). The device may include detection chambers for in-cartridge imaging of fluorescence signal generated during Real-Time PCR amplification (i.e. SYBR green, Taqman, Molecular Beacons), as well as capillary electrophoresis channels for on-device separation and detection of reactions products (amplicons and ligation products). In a preferred embodiment, the capillary electrophoresis channel can be molded in a plastic substrate and filled with a sieving polymer matrix (POP-7™ from Applied Biosystems). Channels containing non-sieving matrix can also be used with properly designed probe sets.

In a preferred embodiment, the devices of the invention comprise liquid handling components, including components for loading and unloading fluids at each station or sets of stations. The liquid handling systems can include robotic systems comprising any number of components. In addition, any or all of the steps outlined herein may be automated; thus, for example; the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtitler plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of heat exchangers such as controlled blocks or platforms to provide accurate temperature control of incubating samples from 0.degree. C. to 100.degree. C.; this is in addition to or in place of the station thermocontrollers.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In a preferred embodiment, useful detectors include a microscope(s) with multiple channels of fluorescence; plate readers to provide fluorescent, electrochemical and/or electrical impedance analyzers, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; capillary electrophoresis systems, mass spectrometers and a computer workstation.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

Kits

In another aspect of the invention, a kit for the routine detection of a predetermined set of nucleic acid targets is produced that utilizes probes, techniques, methods, and a chemical ligation reaction as described herein as part of the detection process. The kit can comprise probes, target sequences, instructions, buffers, and/or other assay components.

Chemical Ligation Dependent Probe Amplification (CLPA)

In another embodiment, the invention relates to chemical ligation dependent probe amplification (CLPA) technology. CLPA is based on the chemical ligation of target specific oligonucleotide probes to form a ligation product. This ligation product subsequently serves as a template for an enzymatic amplification reaction to produce amplicons which are subsequently analyzed using any suitable means. CLPA can be used for a variety of purposes including but not limited to analysis of complex gene signature patterns. Unlike other techniques such as DASL (Bibikova, M., et al., American Journal of Pathology, (2004), 165:5, 1799-1807) and MLPA (Schouten, U.S. Pat. No. 6,955,901) which utilize an enzymatic ligation reaction, CLPA uses a chemical ligation reaction.

In one embodiment, the CLPA assay comprises the use of oligonucleotide probe pairs that incorporate reactive moieties that can self-ligate when properly positioned on a target sequence. In a preferred embodiment, a 3'-phosphorothioate moiety on one probe reacts with a 5'-DABSYL leaving group on the other probe (See Scheme 1 and FIG. 6).

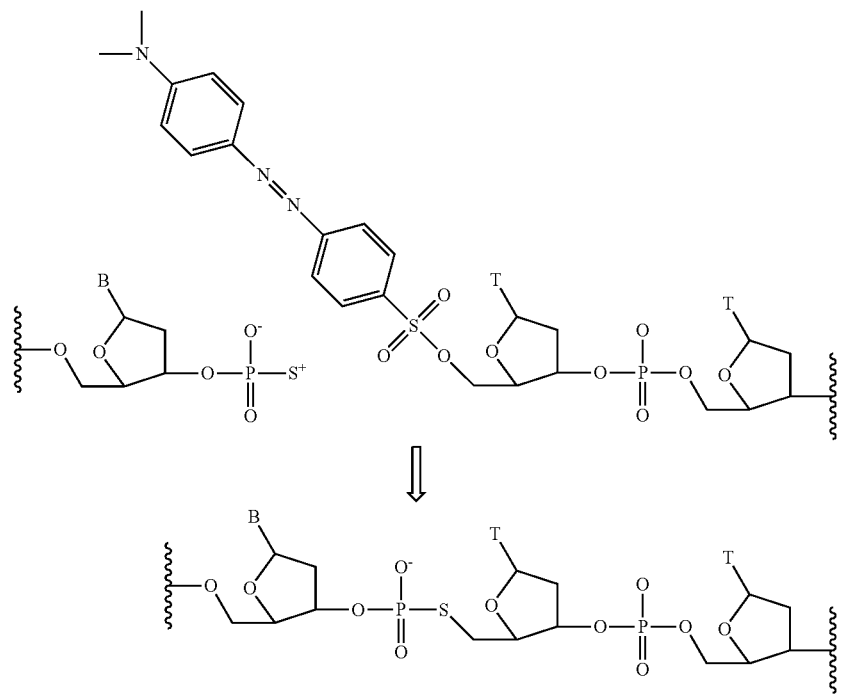

Scheme 1: Chemical Ligation Reaction Between a 3' Phosphorothioate Oligonucleotide (S-Probe) and a 5' DABSYL Modified Oligonucleotide (L-Probe).

The 5'-DABSYL group reacts about four times faster than other moieties, e.g. iodine, and also simplifies purification of the probes during synthesis.

CLPA has several distinct advantages over other sequence-based hybridization techniques. First, CLPA can be applied directly to RNA analysis without the need to make a DNA copy beforehand. Second, CLPA is relatively insensitive to sample contaminants and can be applied directly to impure samples including body samples such as blood, urine, saliva and feces. Third, CLPA involves fewer steps than other known methods, thereby reducing the time required to gain a result. Moreover, CLPA probes can be stored dry, and properly designed systems will spontaneously react to join two or more oligonucleotides in the presence of a complementary target sequence. Chemical ligation reactions show excellent sequence selectivity and can be used to discriminate single nucleotide polymorphisms.

Significantly, unlike enzymatic ligation methods, CLPA shows nearly identical reactivity on DNA and RNA targets which, as described more fully below, renders CLPA more efficient that other known systems, and expands the scope of applications to which CLPA can be utilized.

Advantageously, the CLPA assay reduces the number of steps required to achieve a result, which provides the potential to achieve results in significantly shorter time periods. For example, the general process flow for a standard reverse transcriptase (RT)-multiplex ligase-dependent probe ligation (MLPA) involves the following steps:

1. Isolate total RNA.
2. Use Reverse Transcriptase to make cDNA copy.
3. Hybridize MLPA probe sets to the cDNA target overnight.
4. Add DNA Ligase to join target-bound probes.
5. Amplify ligated probes, e.g. PCR amplification using Taq polymerase and fluorescently labeled PCR primers.
6. Analyze the sample, for example, by CE.

Unlike standard RT-MLPA, CLPA enables analysis to be carried out directly on cell and blood lysates and on RNA targets. Thus, unlike a RT-MLPA, CLPA avoids the necessity of having to isolate the RNA, and then perform reverse transcription to make a cDNA copy prior to ligation. This shortens the time for achieving a result and provides a means to achieve faster analysis.

A further advantage of CLPA is that incorporation of a capture moiety on one probe enables a rapid and specific method for purification of the resulting ligation product from the crude sample free of all impurities and non-target nucleic acid materials, as described below for a biotin-labeled probe. This capability is particularly advantageous in applications where the target nucleic acid is found in the presence of a large excess of non-target nucleic acid, such as in detection of infectious agents (bacteria, fungi, viruses). In this case, the presence of large amounts of host nucleic acid requires use of a high-capacity extraction method, which in turn can result in inefficient amplification of the target nucleic acid due to large amounts of non-target nucleic acid and/or carry-over of inhibitory contaminants.

In another embodiment of this aspect of the invention, faster reaction times are further facilitated by driving the hybridization reaction with higher probe concentrations. Thus, for example, input probe sets may be incorporated in the CLPA reaction at relatively high concentrations, for example, approximately 100-fold higher than those typically used in an MLPA reaction. Elevating the probe concentration significantly reduces the time required for the hybridization step, typically from overnight to between about 15 minutes to about 1 hour.

When higher probe concentrations are used it is generally preferred to incorporate a purification step prior to amplification, especially for high multiplex analysis (e.g. greater than about 5 targets). In one embodiment of this aspect of this invention, a solid support based capture methodology can be employed including membrane capture, magnetic bead capture and/or particle capture. In a preferred embodiment, a biotin/streptavidin magnetic bead purification protocol is employed after ligation and prior to enzymatic amplification. In some instances, the magnetic particles can be directly added to the amplification master mix without interfering with the subsequent amplification reaction. In other instances, it is preferable to release the captured oligonucleotide from the beads and the released oligonucleotide solution is subsequently amplified without the capture particle or surface being present.

In a preferred embodiment, CLPA involves hybridization of a set of probes to a nucleic acid target sequences such that the probes can undergo self-ligation without addition of a ligase. After a ligation product is produced, amplification is generally preferred to facilitate detection and analysis of the product. For this purpose, probes are preferably designed to incorporate PCR primers such as, e.g. universal PCR primers. In a preferred embodiment, the universal primers are not added until after the ligation portion of the reaction is complete, and the primers are added after surface capture purification along with the polymerase, often as part of a PCR master mix.

The CLPA probes possess reactive moieties positioned such that when the CLPA probes are bound to the nucleic acid target, the reactive moieties are in close spatial orientation and able to undergo a ligation reaction without the addition of enzyme. In a preferred embodiment, the chemical ligation moieties are chosen so as to yield a ligated reaction product that can be efficiently amplified by the amplification enzyme which is often a DNA polymerase. Without being bound by theory, chemical ligation chemistries and probe set designs that produce reaction products that more closely resemble substrates that are known as being able to be amplified by DNA and RNA polymerases are more likely to yield efficient probe sets that can be used in the CLPA assay. Especially preferred reaction chemistries are chemical moieties that yield reaction products that closely resemble native DNA such as illustrated in Scheme 1 involving a reaction between a 3'-phosphorothioate and a 5' DABSYL leaving group. In another preferred embodiment, probes sets comprise a 3'-diphosphorothioate (Miller, G. P. et al, Bioorganic and Medicinal Chemistry, (2008) 16:56-64) and a 5'-DABSYL leaving group.

The CLPA probes also incorporate a stuffer sequence (also referred to herein as a variable spacer sequence) to adjust the length of the ligation product. As described further below, length variation provides a convenient means to facilitate analysis of ligation product(s). The stuffer can be located on either probe, though for convenience it is generally incorporated on the S probe (3'-phosphorothioate probe).

In one embodiment of this aspect of the invention, CLPA-CE, the stuffer sequence is varied in length in order to produce one or more variable length ligation products which provide the basis for detection and identification of specific target sequences based on length variation. In a preferred embodiment, variable length ligation products are analyzed by capillary electrophoresis (CE). Generally stuffer sequences are included such that the length of different ligation products varies in a range of at least 1 base pair to about 10 base pairs; preferably from 1 base pair to 4 base pairs. In a preferred embodiment, the length of the different ligation products vary from approximately 80 bp to about 400 bp; preferably in a range of about 100 bp to about 300 bp; more preferably in a range of about 100 bp to about 200 bp In another embodiment, CLPA probes may also contain other optional element(s) to facilitate analysis and detection of a ligated product. For example, it is preferred that one of the probes for use in an embodiment herein referred to as CLPA-MDM incorporate an array binding sequence to bind to an appropriate capture sequence on a microarray platform. For CLPA-MDM, the different CLPA reaction products are not separated by size differences but by the differences in the array binding sequence. In this embodiment, the sequence of the array binding sequence is varied so that each CLPA probe will bind to a unique site on a DNA microarray. The length of the array binding sequence in CLPA-MDM usually varies from 15 to 150 bases, more specifically from 20 to 80 bases, and most specifically from 25 to 50 bases. In some embodiments, CLPA probes preferably also include other elements to facilitate purification and/or analysis including but not limited to labels such as fluorescent labels and hapten moieties such as, for example, biotin for purifying or detecting ligation product(s). For example, probes and/or ligation product(s) that incorporate biotin can be purified on any suitable avidin/streptavidin platform including beads. While biotin/avidin capture systems are preferred, other hapten systems (e.g. Digoxigenin (DIG) labeling) can be used, as can hybridization/oligonucleotide capture. Hybridization/oligonucleotide capture is a preferred method when it is desirable to release the capture product from the beads at a later stage. In addition to magnetic beads, anti-hapten labeled supports (filter paper, porous filters, surface capture) can be used.

CLPA probe-labeling can be on either probe, either at the end or internally. Preferably biotin is incorporated at the 5' end on the phosphorothioate (S-probe).

CLPA probes are generally incorporated in a reaction at a concentration of 250 nanomolar (nM) to 0.01 pM (picomolar) for each probe. Generally, the concentration is between about 1 nM to about 1 pM. Factors to consider when choosing probe concentration include the particular assay and the target being analyzed. The S- or phosphorothioate or Nucleophile probe and L- or leaving group or DABSYL containing probes are incorporated at a concentration that equals or exceeds the concentration of the target. Total concentration of S- and L-probes can reach as high as 10 micromolar (uM). As a non-limiting example, 1 nM for each S and L probe×250 CLPA probe pairs would equal 500 nm (1 nm per probe×2 probes per pair×250 targets) at 10 nM for each probe would mean a total concentration of 5 uM.

The target concentration usually ranges from about 10 micrograms of total RNA to about 10 nanograms, but it can be a little as a single copy of a gene.

Figure 2:
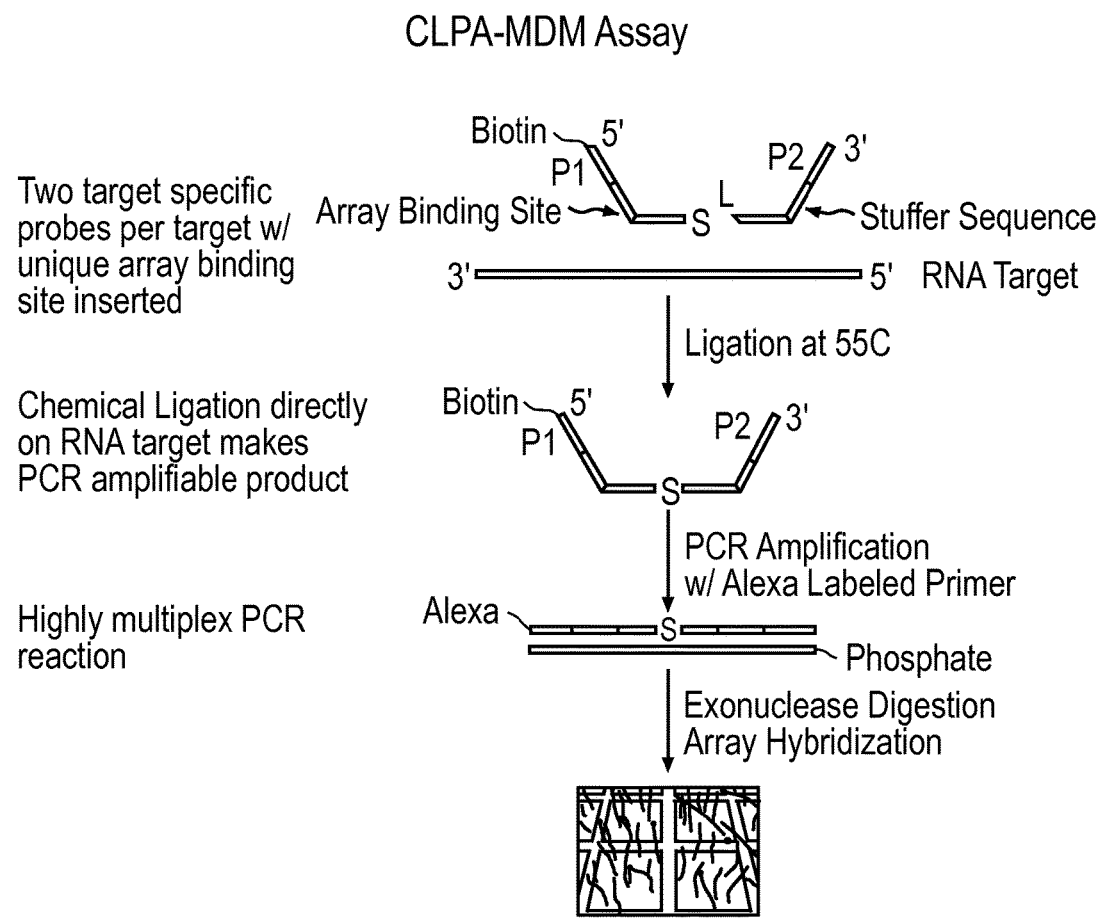
FIG. 2. Schematic representation of one embodiment of CLPA-MDM assay.
Figure 3:
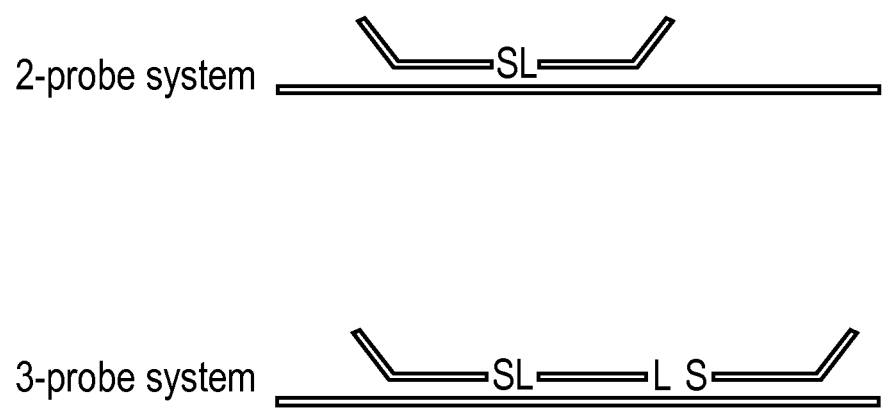
FIG. 3. Schematic representation showing one embodiment of the 2-probe and the 3-probe CLPA reaction.

In a preferred embodiment of CLPA technology, a CLPA probe set consists of 2 oligonucleotide probes with complementary reactive groups (FIGS. 1 and 2). In another embodiment, the CLPA probe set may consist of 3 or more probes that bind adjacent to each other on a target. In a preferred embodiment of the 3-probe CLPA reaction, the outer probes are designed to contain the enzymatic amplification primer binding sites, and the inner probe is designed to span the region of the target between the other probes. In a more preferred embodiment, the outer probes have non-complementary reactive groups such that they are unable to react with each other in the absence of the internal (middle) probe (FIG. 3). In some instances, both outer probes may have similar reactive moieties except that one group is at the 5' end of one probe and the 3'-end of the other probe, and the L-probe chemistries may also be similar to each other except for positioning on the probe. As is known to one who is skilled in the art, different chemical reagents and processes may be needed to manufacture the probes for the 3-probe CLPA reaction compared to the probes for the 2-probe CLPA system.

Figure 4:
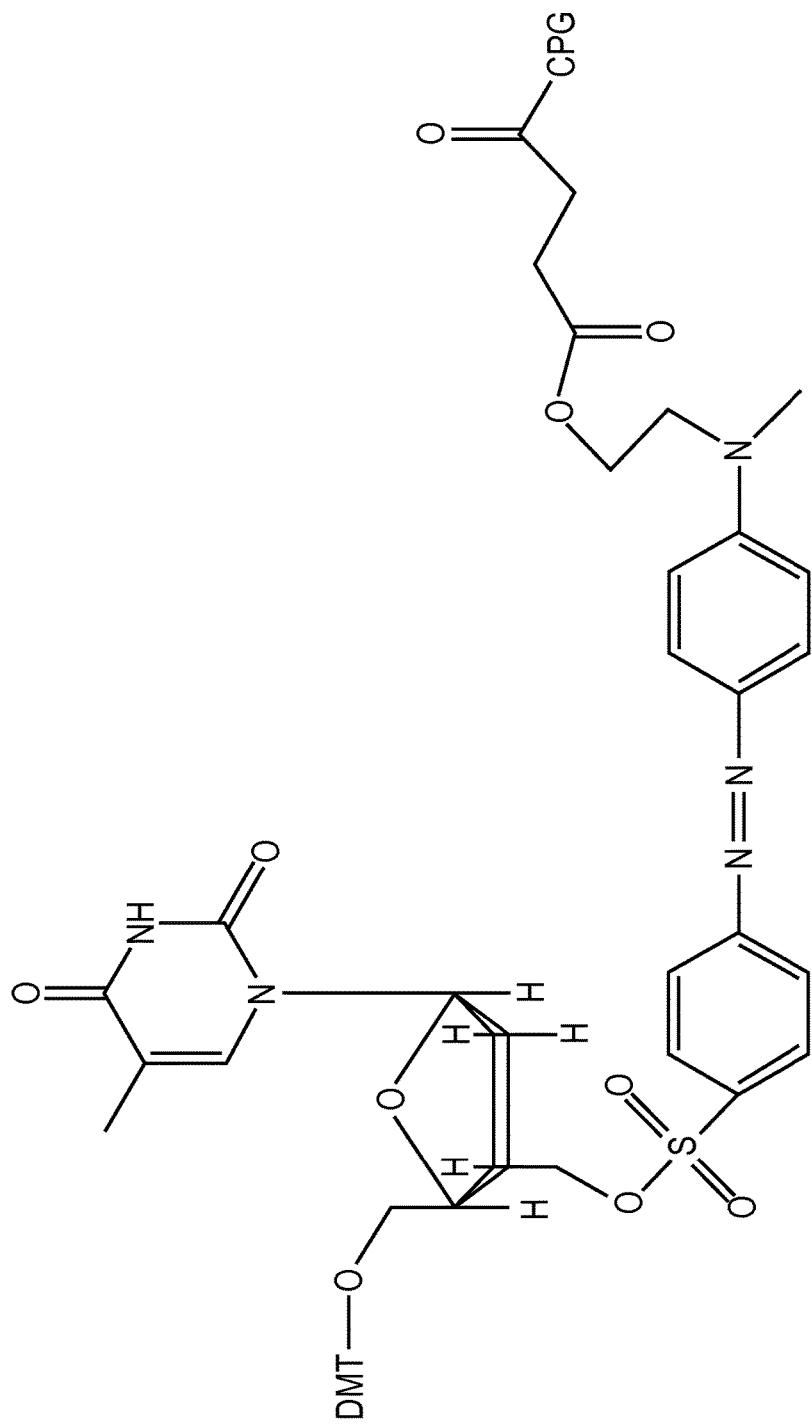
FIG. 4. Schematic Representation of a DNA synthesis resin that can be used to manufacture DNA with a 3'-DABSYL leaving group FIG. 5. Schematic Representation on the process flow for one embodiment of the CLPA-CE assay FIG. 6. Schematic chart showing probe design for CLPA assay in which is incorporated a size-variant stuffer sequence.
Figure 5:
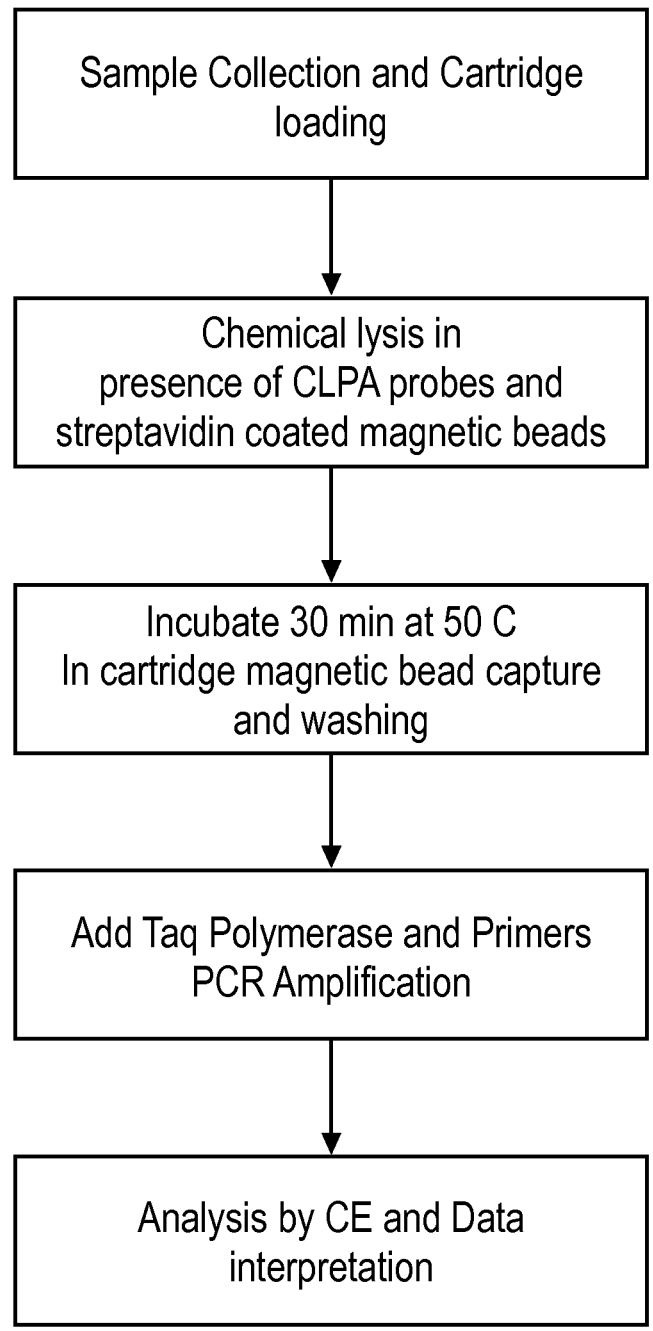

In a preferred embodiment of the 3-probe CLPA system, one outer probe contains a 3' phosphorothioate (3'S-probe), the other outer probe contains a 5'-phosphorothioate (5'-S-probe) and the center probe contains both a 3'- and a 5'-DABSYL leaving group. The manufacture of a 5'-DABSYL leaving group probes has been reported previously (Sando et al, J. Am. Chem. Soc., (2002), 124(10) 2096-2097). We recently developed a new DNA synthesis reagent that allows for the routine incorporation of a 3'-DABSYL leaving group (FIG. 4).

CLPA-CE

Figure 6:
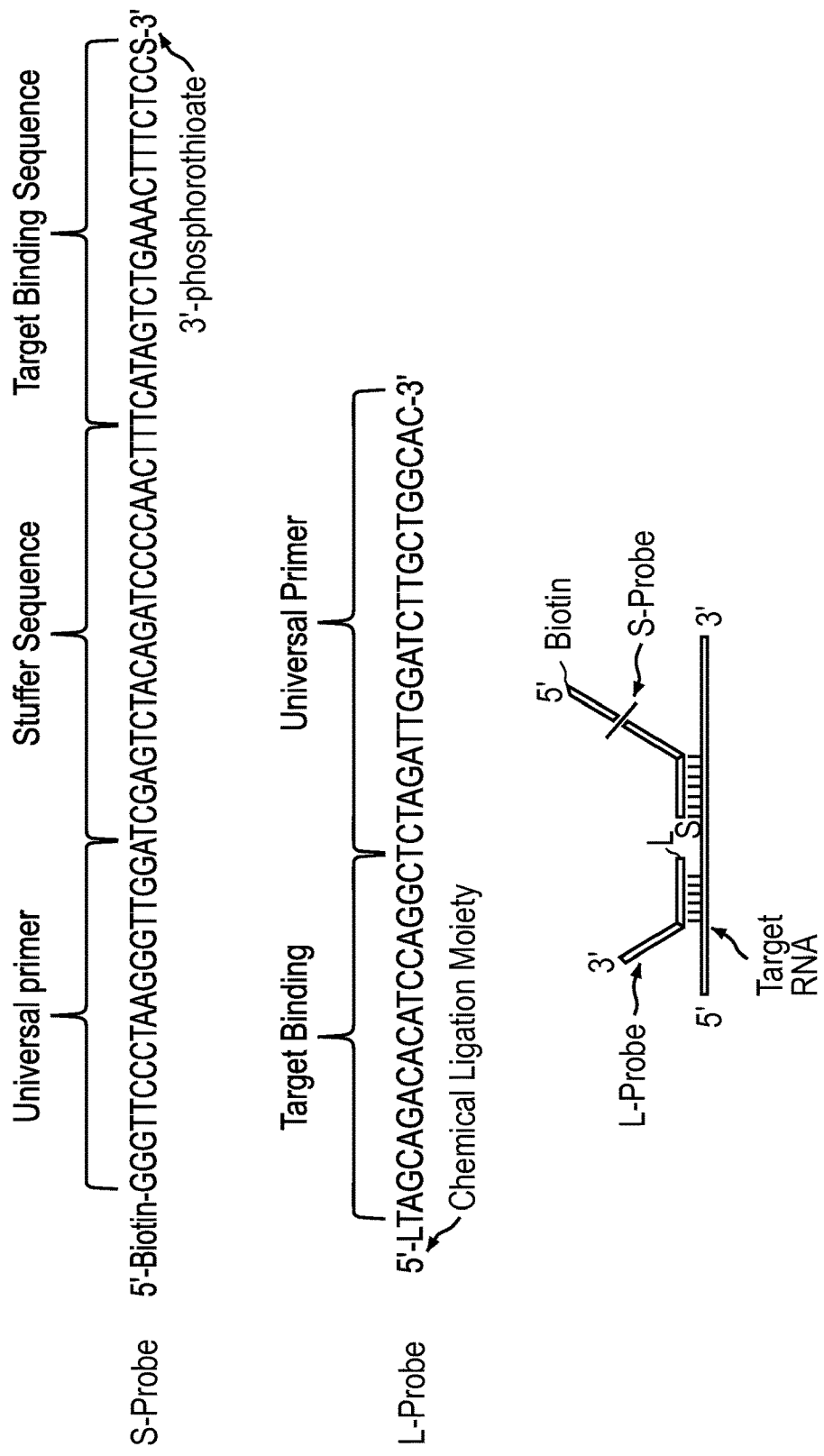
Figure 6 discloses SEQ ID NOS 8 and 10, respectively, in order of appearance.

In one embodiment, CLPA ligation product(s) are detected by size differentiation capillary electrophoresis (CE) on a sieving matrix, or by slab gel electophoresis. A schematic representation for CLPA-CE is provided in FIG. 1. In this example, analysis is performed directly on a blood sample following cell lysis by any appropriate means including chemically, mechanically or osmotically, and addition of appropriately designed probes. In a preferred embodiment, chemical lysis of the cells is used FIG. 6 provides a general schematic representation of the design of a probe set for CLPA-CE analysis. In this example the S probe is designed to include a universal PCR primer for subsequent amplification of ligation product(s); a stuffer sequence which is designed with a length that correlates with a specific target; and a target binding sequence. Likewise, the L-probe includes a target binding sequence and universal primer. The probes are usually labeled with a fluorophore (FAM, Cy3, Cy5, etc), however they can also be detected without fluorescence labeling. The labeling is done by using a fluorescently labeled PCR primer.

Figure 7:
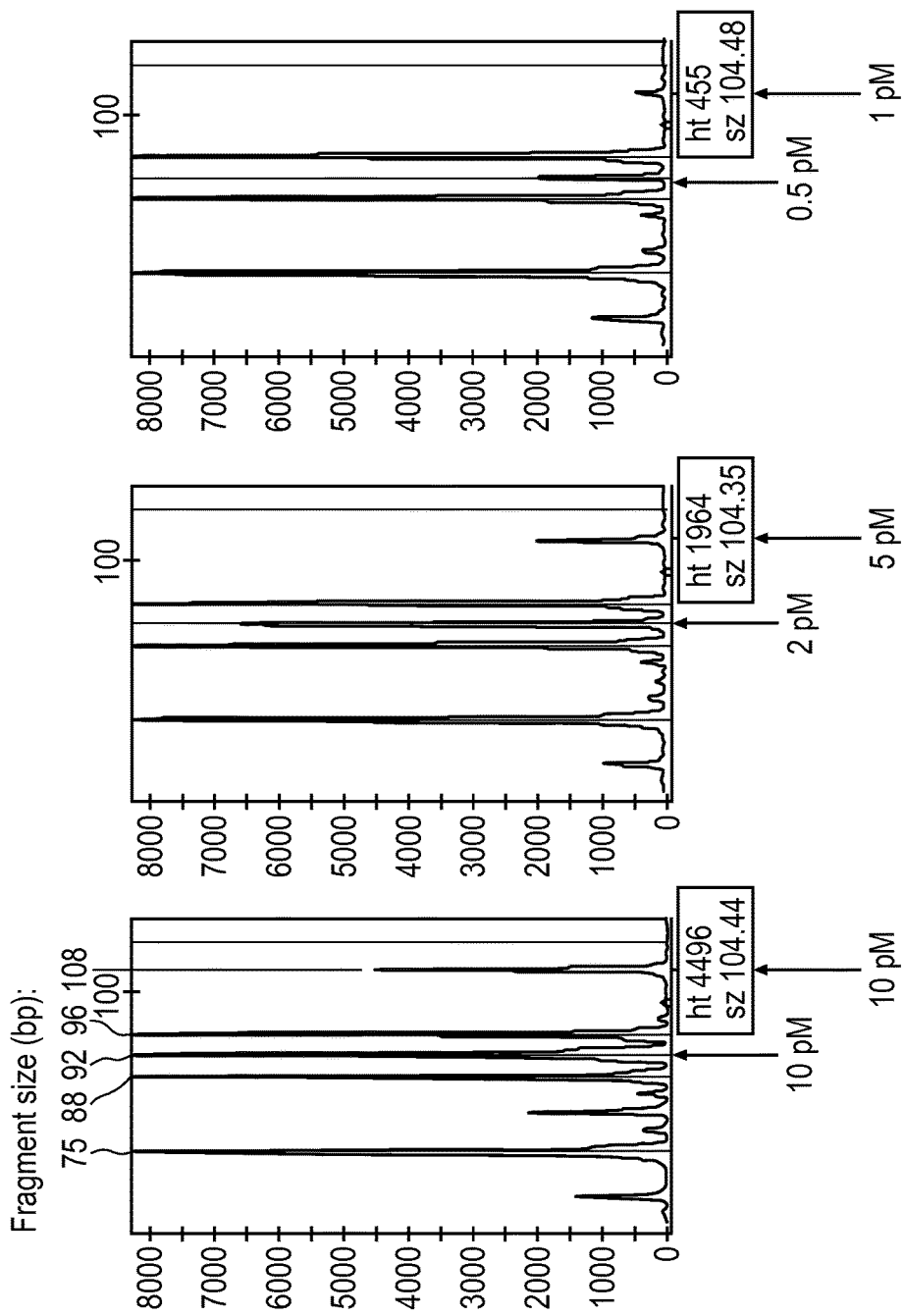
FIG. 7. Electrophoretic separation profile on sample analyzed by CLPA-CE.

In this example of CLPA-CE probes, the S probe also includes a biotin moiety at the 5' end to facilitate purification and removal of unligated probe. Following amplification of ligated product(s), each having a unique length, the reaction mixture is separated by CE, or other suitable size separation technique. The peak height or intensity of each product is a reflection of target sequence expression, i.e. level of target in the sample. (FIG. 1 and FIG. 7).

CLPA-MDM

In another embodiment of this aspect of the invention, CLPA ligation products are analyzed/detected by microarray analysis (CLPA-MDM). A schematic representation of CLPA-MDM is provided in FIG. 2. CLPA-MDM differs from CLPA-CE in at least the following respects. First, the probe sets differ in design. For example, a general representation of a CLPA-MDM probe set is depicted in FIG. 2. As with CLPA-CE probes, CLPA-MDM probe sets can include universal primers for amplification of ligation product(s). They also include target specific sequences, as well as ligation moieties for enzyme-independent ligation. Additionally, CLPA-MDM probes also may include a stuffer sequence, however the purpose of this stuffer sequence is to adjust the size of the CLPA-MDM to the same length in an effort to standardize enzymatic amplification efficiency. Normalization of amplicon size is not a requirement but a preferred embodiment. A second difference between the design of CLPA-CE and CLPA-MDM probe sets is that the latter include a unique array binding sequence for use with an appropriate microarray platform.

In respect of the CLPA-MDM aspect of the invention, a microarray binding site (ABS sequence) is incorporated into the probe designs for use with a "universal" microarray platform for the detection. Similar to the CLPA-CE system, probes are preferably labeled with a fluorophore, for example by using a fluorescently labeled PCR primer. Alternatively, for example, a sandwich assay labeling technique can be used for the final read-out. Sandwich assays involve designing the probes with a common (generic) label binding site (LBS) in place or in addition to the stuffer sequence and using a secondary probe that will bind to this site during the array hybridization step. This methodology is particularly useful when it is desirable to label the arrays with a chemiluminescent system like a horse radish peroxidase (HRP) labeled oligonucleotide, or with an electrochemical detection system. Generally, planar microarrays are employed (e.g. microarrays spotted on glass slides or circuit board) for the read-out. However, bead microarrays such as those available from Luminex and Illumina can also be used (e.g. Luminex xMAP/xtag).

EXAMPLE 1

Quantitative Multiplex Detection of 5 Targets

Figure 8:
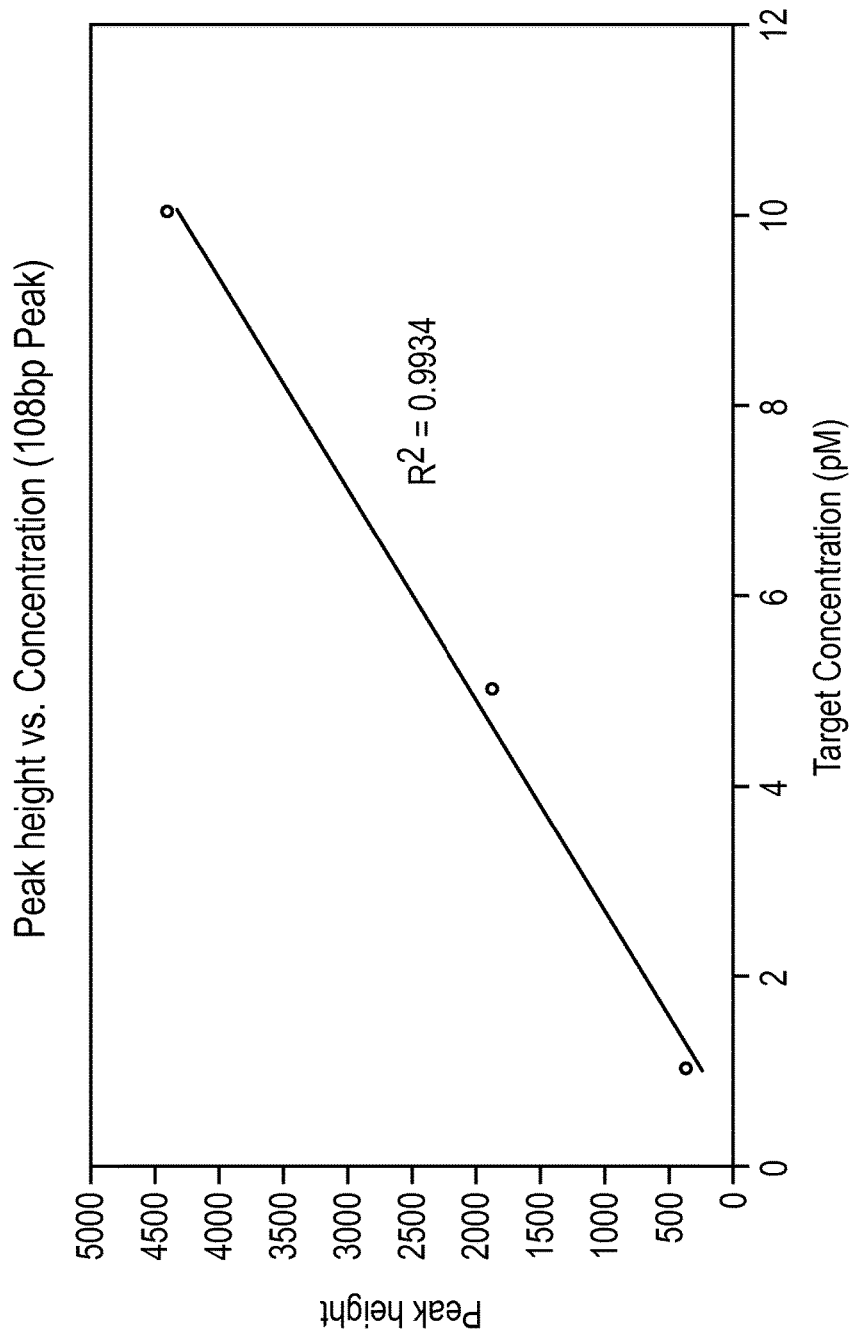
FIG. 8. Linear relationship between target concentration and peak height in CLPA-CE analysis.

Multiplex CLPA reactions were performed using five (5) DNA target mimics (corresponding to portions of the MOAP1 (SEQ ID NO:5), PCNA (SEQ ID NO:9), DDB2 (SEQ ID NO:12), BBC3 (SEQ ID NO:16) and BAX (SEQ ID NO:19) genes) combined in one reaction in the presence of their respective CLPA probes (Table 1) (S and L probes at 1 nM each). The target mimics were pooled in different concentration as shown in Table 2. The target mimics, S probes and L probes were incubated in PCR buffer (1× PCR buffer is 1.5 mM MgCL2, 50 mM KCl, 10 mM Tris-HCl pH8.3) for 1 hour at 50 C. A 1 ul aliquot of each reaction mixture was used as template for PCR amplification using Dynamo SYBR green PCR mix in the presence of Universal Primers (SEQ ID NOS 1 and 2, 300 nM). The samples were PCR cycled for 27 cycles (95 C 15 min followed by 27 cycles of 95 C (10 s), 60 C (24 s), 72 C (10 s). After PCR amplification, the samples were denatured and injected into an ABI 3130 DNA sequencer (capillary electrophoresis instrument). The CE trace from the ABI for the 3 samples as well as a plot of the peak versus target mimic concentration of PCNA is shown in FIG. 7 and a plot of the linear response of the signal of PCNA as a function on input concentration is shown in FIG. 8.

TABLE 1.

Probe and target sequence information.

| SEQ ID | Name | Sequence Detail | Amplicon Size |
|---|---|---|---|
| 1 | Forward PCR Primer | FAM-GGGTTCCCTAAGGGTTGGA | |
| 2 | Reverse PCR Primer | GTGCCAGCAAGATCCAATCTAGA | |
| 3 | MOAP 1 -L | LTACATCCTTCCTAGTCAATTACACTCTAGATTGGA TCTTGCTGGCAC | |
| 4 | MOAP1-S | 5'-Biotin-GGGTTCCCTAAGGGTTGGATAGGTAAAT GGCAGTGTAGAACS | 41 |
| | | Ligated MOAP1 Amplicon | 88 |
| 5 | MOAP1-Target mimic | GTGTAATTGACTAGGAAGGATGTAGTTCTACACTG CCATTTACCTA | |
| 6 | MOAP1-RNA Target mimic | GUGUAAUUGACUAGGAAGGAUGUAGUUCUACAC UGCCAUUUACCUA | |
| 7 | PCNA-L | LTGGTTTGGTGCTTCAAATACTCTCTAGATTGGATC TTGCTGGCAC | 45 |
| 8 | PCNA-S | Biotin-GGGTTCCCTAAGGGTTGGATCGAGTCTACAGATCC CCAACTTTCATAGTCTGAAACTTTCTCCS | 63 |
| | | Ligated PCNA Amplicon | 108 |
| 9 | PCNA-Target Mimic | AGTATTTGAAGCACCAAACCAGGAGAAAGTTTCA GACTATGA | |
| 10 | DDB2-L | LTAGCAGACACATCCAGGCTCTAGATTGGATCTTG CTGGCAC | 51 |
| 11 | DDB2-S | Biotin-GGGTTCCCTAAGGGTTGGATCGAGTCTACTCCAAC TTTGACCACCATTCGGCTACS | 49 |
| | | Ligated DDB2 Amplicon | 96 |
| 12 | DDB2-Target Mimic | GCCTGGATGTGTCTGCTAGTAGCCGAATGGTGGTC A | |
| 13 | DDB2-RNA Target Mimic | GCCUGGAUGUGUCUGCUAGUAGCCGAAUGGUGG UCA | |
| 14 | BBC3-L | LTCCGAGATTTCCCCCTCTAGATTGGATCTTGCTGG CAC | 38 |
| 15 | BBC3-S | Biotin-GGGTTCCCTAAGGGTTGGATCCCAGACTCCTCCCT CTS | 37 |
| | | Ligated BBC3 Amplicon | 75 |
| 16 | BBC3-Target Mimic | GGG G GG G GGA AAT CTC GGA AGA GGG AGG AGT CTG GG | |
| 17 | BAX-L | LTCACGGTCTGCCACGCTCTAGATTGGATCTTGCTG GCAC | 39 |

TABLE 1.-continued

Probe and target sequence information.

| SEQ ID | Name | Sequence Detail | Amplicon Size |
|---|---|---|---|
| 18 | BAX-S | Biotin-GGGTTCCCTAAGGGTTGGA TGA GTC TAC ATGA TC CT TCCCGCCACAAAGATGGS | 53 |
| | | Ligated BAX Amplicon | 92 |
| 19 | BAX-Target Mimic | CGTGGCAGACCGTGACCATCTTTGTGGCGGGA | |
| 20 | 3-phosphorothioate GAPDH | Biotin-GGGTTCCCTAAGGGTTGGACGGACGCCTGCTTCAC CACCTTCTTGATGTCAS | 51 |
| 21 | Middle 2L probe GAPDH | LTCATATTTGGCAGGTTTTTCTAGACGGCAGGTL | 32 |
| 22 | 5'-phosphorothioate GAPDH | SCAGGTCCACCACTGACACGTTGGCAGTTCTAGAT TGGATCTTGCTGGCAC | 50 |
| | | Ligated 3-probe amplicon | 133 |
| 24 | GAPDH Target Mimic | ACT GCC AAC GTG TCA GTG GTG GAC CTG ACC TGC CGT CTA GAA AAA CCT GCC AAA TAT GAT GAC ATC AAG AAG GTG GTG AAG CAG GCG TC | |
| 25 | GAPDH 3-L | LTTTTTCTAGACGGCAGGTCAGGTCCACCAGATGAT CGACGAGACACTCTCGCCATCTAGATTGGATCTTG CTGGCAC | |
| 26 | GAPDH 3-S | GGGTTCCCTAAGGGTTGGACGGACCAACTCCTCGC CATATCATCTGTACACCTTCTTGATGTCATCATATT TGGCAGGTS | |
| 27 | GAPDH-3-FAM/BHQ-1 Taqman Probe | (FAM)ccaactcctcgccatatcatctgtacaccttcttg(BHQ-1) | |
| 28 | GAPDH 4-L | LTGCTGATGATCTTGAGGCTGTTGTCATACTGATG ATCGACGAGACACTCTCGCCATCTAGATTGGATCT TGCTGGCAC | |
| 29 | GAPDH-4-S | GGGTTCCCTAAGGGTTGGACGATGGAGTTGATGCT GACGGAAGTCATAGTAAGCAGTTGGTGGTGCAGG AGGCATS | |
| 30 | GAPDH-4-QUASAR 670/BHQ-2 Taqman Probe | (Quasar 670)tgctgacggaagtcatagtaagcagttggt(BHQ-2) | |
| 31 | PCNA 2-L | LTCCTTGAGTGCCTCCAACACCTTCTTGAGGATGAT CGACGAGACACTCTCGCCATCTAGATTGGATCTTG CTGGCAC | |
| 32 | PCNA 2-S | GGGTTCCCTAAGGGTTGGACGGTACAACAAGACCC AGCTGACGACTCTTAATATCCCAGCAGGCCTCGTT GATGAGGS | |
| 33 | PCNA 2-Cal Fluor Orange 560/BHQ-1 | (CAL Red 610)ctgacgactcttaatatcccagcaggcctcgtt(BHQ-2) | |
| 34 | DDB2-2-L | LTTAGTTCCAAGATAACCTTGGTTCCAGGCTGATG ATCGACGAGACACTCTCGCCATCTAGATTGGATCT TGCTGGCAC | |
| 35 | DDB2-2-S | BiotinGGGTTCCCTAAGGGTTGGACGTTAGACGCCA ATAGGAGTTTCACTGGTGGCTACCACCCACTGAGA GGAGAAAAGTCATS | |
| 36 | DDB2-2-CAL Fluor Orange 560/BHQ-1 | (Cal Orange 560)cgccaataggagtttcactggtggctacca(BHQ-2) | |

L = DABSYL ligation moiety
S = phosphorothiate moiety

TABLE 2

Sample Concentrations

| Sample | Target Mimic Concentrations |
|---|---|
| 1 | All Target mimics at 10 pM final Concentration |
| 2 | MOAP1, DDB2 and BBC3 at 10 pM, PCNA at 5pM and BAX at 2 pM |
| 3 | MOAP1, DDB2 and BBC3 at 10 pM, PCNA at 1pM and BAX at 0.5 pM |

EXAMPLE 2

CLPA Reactions Using MOAP1 and DDB2 DNA and RNA Target Mimics

Reactions were prepared in duplicate as presented in Table 3 using DNA or RNA target mimics for the MOAP1 and DDB2 genes and CLPA probes sets designed to target the sequences. The probe numbers refer to the SEQ ID NOs in Table 1. The reagents were added in the concentrations and volumes shown in Table 4. The respective S-probe, L-probe and target mimic were heated to 50° C. for 60 minutes in a 0.2 mL PCR tube, after which 2.5 µl of the CLPA reaction was used as template in a real-time PCR reaction with 40 amplification cycles. Real-time PCR data was averaged for the duplicate samples and is presented in Table 3 (Ct value column). Minimal differences in Ct value between RNA and DNA target mimics were observed indicating similar probe ligation efficiency on RNA and DNA substrates.

TABLE 3

CLPA Probe Sets.

| Sample | Identifier | L-Probe (1 nM) SEQ ID NO | S-Probe (1 nM) SEQ ID NO | Target Mimic (10 pM) SEQ ID NO | Ct value |
|---|---|---|---|---|---|
| 1 | MOAP-1 DNA | 3 | 4 | 5 | 19.5 |
| 2 | MOAP-1 RNA | 3 | 4 | 6 | 20 |
| 3 | DDB2 DNA | 10 | 11 | 12 | 21 |
| 4 | DDB2 RNA | 10 | 11 | 13 | 21 |

TABLE 4

Reagent table-Example 1

| | |
|---|---|
| 1X PCR Buffer Buffer* | 12.5 ul |
| S-Probe (1 nM) & L-Probe (1 nM) | 2.5 ul each |
| Target Mimic (100 pM) | 2.5 ul |
| Water | 5.0 ul |

Heat at 50 C. for 1 hour
*1X PCR buffer is 1.5 mM MgCL2, 50 mM KCl, 10 mM Tris-HCl pH 8.3

EXAMPLE 3

Direct Analysis of DDB2 RNA Transcripts in Lysis Buffer and Lysed Blood

DDB2 messenger RNA (mRNA) was prepared using a in-vitro transcription kit from Ambion and a cDNA vector plasmid from Origene (SC122547). The concentration of mRNA was determined using PicoGreen RNA assay kit from invitrogen. The DDB2 probe sets (Table 5) were tested with different concentrations of DDB2 mRNA transcript spiked into either water or whole blood. The reactions mixture components are listed in Table 5. Samples 1-4 consisted of DDB2 transcript at 10 ng, 1 ng, 0.1 ng and 0.01 ng in water, and samples 5-8 consisted of the same concentration range spiked into whole blood. Similar reactions protocols were followed with the exception of adding Proteinase K to the blood samples so as to reduce protein coagulation. The procedure is as follows: The reagents were added in the concentrations and volumes in Table 5. The S-probes, mRNA transcript, Guanidine hydrochloride lysis buffer and either water (samples 1-4) or whole blood (samples 5-8) were heated to 80° C. for 5 minutes and then they were moved to a 55° C. heat block. The L-probe, wash buffer, streptavidin beads and proteinase K were added, and the reaction was incubated at 55° C. for 60 minutes. The samples were removed from the heat block and the magnetic beads were captured using a dynal MPC 96S magnetic capture plate. The supernatant was removed and the beads were washed 3 times with wash buffer. DyNamo SYBR green PCR master mix (25 ul, 1×) and universal primers (SEQ ID NOS 1 and 2, 300 nM) were added to the beads and samples were heat cycled using a Stratagene MX4000 realtime PCR instrument for 30 cycles (95° C. for 15 minutes, 30 cycles 95° C. (10 s), 60°C. (24 s), 72° C. (10 s)). The Ct values were recorded and the amplified samples were injected into an Agilent Bioanalyzer 2100 so as to verify the length of the amplicons. All amplicons showed the correct size (~96 bp) and the performance was comparable for the blood and water samples demonstrating the ability to directly analyze RNA in lysed blood. The results are summarizes in Table 7 below.

TABLE 5

CLPA Probe Sets.

| Sample | Identifier | L-Probe (1 nM) | S-Probe (1 nM) | RNA Transcript |
|---|---|---|---|---|
| 1-8 | DDB2 | SEQ ID NO: 10 | SEQ ID NO: 11 | Origene Plasmid SC122547 |

TABLE 6

DDB2 reaction mixture.

| | Samples | |
|---|---|---|
| | 1-4 | 5-8 |
| GuHCL Lysis Buffer (2X) | 12.5 µl | 12.5 µl |
| S-Probe (5 nM) | 1 µl | 1 µl |
| RNA Transcript (10 ng/ul to 0.01 ng/ul) | 1 µl | 1 µl |
| Whole Blood | 0 µl | 12.5 µl |
| Water | 12.5 ul | 0 µl |
| Heat 80° C. for 5 min, chill on ice | | |
| Wash Buffer | 20 µl | 15 µl |
| L-Probe (5 nM) | 1 µl | 1 µl |
| Dynal M-270 Beads | 2 µl | 2 µl |
| Proteinase K (10 mg/ml) | 0 µl | 5 µl |
| Total | 50 µl | 50 µl |

Incubate 55° C. for 60 min.
a) GuHCL lysis buffer (1X) is 3M GUHCL, 20 mM EDTA, 5 mM DTT, 1.5% Triton, 30 mM Tris pH 7.2).
b) Wash Buffer is 100 mM Tris (pH 7.4), 0.01% Triton.

TABLE 7

Summary results of water versus blood

| Assay | DDB2 Conc | Ct value | Sample |
|---|---|---|---|
| 1 | 10 ng | 13.5 | Water |
| 2 | 1 ng | 17 | Water |
| 3 | 0.1 ng | 20.2 | Water |
| 4 | 0.01 ng | 24 | Water |
| 5 | 10 ng | 13.5 | Blood |
| 6 | 1 ng | 16 | Blood |
| 7 | 0.1 ng | 19.2 | Blood |
| 8 | 0.01 ng | 23.5 | Blood |

EXAMPLE 4

3-Probe CLPA-CE Assay

Reactions were prepared in duplicate as presented in Table 8 using DNA target mimic probe SEQ ID NO 24 and the 3-probe CLPA probe set (SEQ ID NOS 20, 21 and 22). The probe numbers refer to the SEQ ID NOS in Table 1. The reagents were added in the concentrations and volumes in Table 9. The S-probes, L-probe and target mimics were heated to 50° C. for 60 minutes in a 0.2 mL PCR tube, after which 2.5 µl of the CLPA reaction was used as template in a Dynamo SYBR green PCR reaction with 25 amplification cycles. Real-time PCR data was averaged for the duplicate samples and is presented in Table 8 (Ct value column). A 1 µl sample of each reaction was then analyzed via Agilent Bioanalyzer 2100 to determine the size of the reaction product.

TABLE 8

CLPA Probe Sets.

| Samples | Identifier | 3'-S probe SEQ ID NO | 2L- Probe SEQ ID NO | 5'-S Probe SEQ ID NO | Target Mimic SEQ ID NO | Amplicon size | Ct value |
|---|---|---|---|---|---|---|---|
| 1 & 2 | GAPDH | 20 | 21 | 22 | 23 | About 135 bp | 16.3 |
| 3 & 4 | Negative | 20 | 21 | 22 | 23 | None observed | No CT |

Probes at 1 nM concentration; target mimic at 10 pM concentration.

TABLE 9

Reagent table-Example 1

| | |
|---|---|
| 1X PCR Buffer Buffer* | 12.5 µl |
| 3 and 5' S-Probe (10 nM) & 2L-Probe (10 nM) | 2.5 µl each |
| Target Mimic (1 nM) | 2.5 µl |
| Water | 2.5 µl |

Heat at 50 C. for 1 hour
*1X PCR buffer is 1.5 mM MgCL2, 50 mM KCl, 10 mM Tris-HCl pH 8.3

EXAMPLE 5

Multiplex Real-Time CLPA Detection of mRNA

In a 0.2 ml PCR tube was added 4 sets of CLPA reagents that were engineered to possess unique binding sites for different color dual labeled probes. The reactions were prepared as indicated in Table 10 and Table 11. The CLPA probes sets and dual labeled probes correspond to SEQ ID NOS 25 through 36 in Table 1. The S and run-off transcript mRNA (GAPDH, PCNA and DDB2) were added to 2× lysis buffer (GuHCL lysis buffer (1×) is 3M GUHCL, 20 mM EDTA, 5 mM DTT, 1.5% Triton, 30 mM Tris pH 7.2) and heated to 80° C. for 5 min. The samples were cooled on ice and streptavidin coated magnetic beads (DYNAL M-270) and L-probe were added. The samples were heated at 50° C. for 1 hour. The magnetic beads were captured on a DYNAL MPC plate and washed twice with wash buffer. The beads were recaptured and dynamo PCR 1× mastermix was added with the 4 different dual labeled probes and universal PCR primers (25 ul total volume). The samples were heat cycled using a Stratagene MX4000 realtime PCR instrument for 30 cycles (95° C. for 15 minutes, 30 cycles 95° C. (10 s), 60° C. (24 s), 72° C. (10 s)) with proper filters for monitoring the fluorescence in the FAM, Cal Fluor orange 560, Cal Fluor Red 610, and Quasar 670 channels. The Ct values observed for each channel were recorded and are indicated in Table 10.

TABLE 10

Multiplex reagents used in Example 5.

| Samples | S Probes (25 pM) SEQ ID NOs | L Probes (25 pM) SEQ ID NOs | Targets | Ct(FAM)-GAPDH3 | Ct(560)-DDB2 | Ct(610)-PCNA | Ct(670)-GAPDH4 |
|---|---|---|---|---|---|---|---|
| 1 & 2 | 26, 29, 32, 35 | 25, 28, 31, 34 | 250 ng yeast tRNA; 40 pg GAPDH(Origene SC118869), 40 pg PCNA (SC118528), 40 pg DDB2 (SC122547) mRNA | 25.5 | 24.5 | 24.8 | 25.8 |
| 3 & 4 | 26, 29, 32, 35 | 25, 28, 31, 34 | 250 ng yeast tRNA (negative) | No Ct | No Ct | No Ct | No Ct |
| 5 & 6 | 26, 29, 32, 35 | 25, 28, 31, 34 | 250 ng yeast tRNA; 40 pg GAPDH(Origene SC118869), 40 pg PCNA (SC118528), 40 pg DDB2 (SC122547) mRNA | 22.1 | 24.5 | 22.1 | 22.2 |
| 7 & 8 | 26, 29, 32, 35 | 25, 28, 31, 34 | 250 ng yeast tRNA (negative) | No Ct | No Ct | No Ct | No Ct |

TABLE 11

Additional reagents used in Example 5.

| | |
|---|---|
| GuHCL Lysis Buffer (2X) | 12.5 µl |
| S-Probes (0.25 nM Stock of each) | 5 µl |
| mRNAs (250 ng tRNA +/− mRNAs) | 5 µl |
| Water | 2.5 µl |
| Heat 80° C. for 5 min, chill on ice | |
| Water | 18 µl |
| L-Probes (0.25 nm stock of each) | 5 µl |
| Beads | 2 µl |
| Total | 50 µl |
| Incubate 50° C. 1 Hour | |

What is claimed is:

1. A method for detecting in a sample, comprising a plurality of sample nucleic acids of different nucleic acid sequences, the presence of at least one specific target nucleic acid sequence comprising a first and a second target domain, the domains located adjacent to one another, comprising the steps of:
   (a) contacting the sample nucleic acids with a plurality of different probes sets, each probe set comprising:
      (i) a first ligation probe comprising:
         (1) a first probe domain complementary to said first target domain;
         (2) a first non-complementary region being non-complementary to the said target nucleic acid sequence; and
         (3) a 5'-ligation moiety comprising a DABSYL moiety; and
      (ii) second ligation probe comprising:
         (1) a second probe domain complementary to said second target domain;
         (2) a second non-complementary region, being non-complementary to the said target nucleic acid sequence;
         (3) a 3' ligation moiety comprising a phosphorothioate moiety;
   (b) ligating said first and second ligation probes in the absence of a ligase enzyme to form a ligation product; wherein at least one of said ligation probes comprises a variable spacer nucleic acid sequence such that each ligation product is a different length;
   (c) amplifying said ligation product to form ligation amplicons under conditions whereby a fluorescent label is incorporated into said amplicons; and
   (d) detecting the presence of said ligation amplicons by detecting the presence of said fluorescent label.

2. A method of claim 1, wherein said target nucleic acid sequence is RNA and/or DNA.

3. A method of claim 1, wherein said target nucleic acid sequence comprises unpurified RNA.

4. A method as in claim 1, wherein said detecting step is by capillary electrophoresis.

5. A method for detecting in a sample, comprising a plurality of sample nucleic acids of different nucleic acid sequences, the presence of at least one specific target nucleic acid sequence comprising a first and a second target domain, the domains located adjacent to one another, comprising the steps of:

(a) contacting the sample nucleic acids with a plurality of different probes sets, each probe set comprising:
  (i) a first ligation probe comprising:
    (1) a first probe domain complementary to said first target domain;
    (2) a first non-complementary region being non-complementary to the said target nucleic acid sequence; and
    (3) a 5'-ligation moiety comprising a halogen leaving group; and
  (ii) second ligation probe comprising:
    (1) a second probe domain complementary to said second target domain;
    (2) a second non-complementary region, being non-complementary to the said target nucleic acid sequence;
    (3) a 3' ligation moiety comprising a phosphorothioate moiety;
(b) ligating said first and second ligation probes in the absence of a ligase enzyme to form a ligation product; wherein at least one of said ligation probes comprises a variable spacer nucleic acid sequence such that each ligation product is a different length;
(c) amplifying said ligation product to form ligation amplicons under conditions whereby a fluorescent label is incorporated into said amplicons; and
(d) detecting the presence of said ligation amplicons by detecting the presence of said fluorescent label.

6. A method of claim 5, wherein said target nucleic acid sequence is RNA and/or DNA.

7. A method of claim 5, wherein said target nucleic acid sequence comprises unpurified RNA.

8. A method as in claim 5, wherein said detecting step is by capillary electrophoresis.

9. A method for detecting in a sample, comprising a plurality of sample nucleic acids of different nucleic acid sequences, the presence of at least one specific target nucleic acid sequence comprising a first and a second target domain, the domains located adjacent to one another, comprising the steps of:
(a) contacting the sample nucleic acids with a plurality of different probes sets, each probe set comprising:
  (i) a first ligation probe comprising:
    (1) a first probe domain complementary to said first target domain;
    (2) a first non-complementary region being non-complementary to the said target nucleic acid sequence; and
    (3) a 5'-ligation moiety comprising a leaving group; and
  (ii) second ligation probe comprising:
    (1) a second probe domain complementary to said second target domain;
    (2) a second non-complementary region, being non-complementary to the said target nucleic acid sequence;
    (3) a 3' ligation moiety comprising a nucleophilic group;
(b) ligating said first and second ligation probes in the absence of a ligase enzyme to form a ligation product; wherein at least one of said ligation probes comprises a variable spacer nucleic acid sequence such that each ligation product is a different length;
(c) amplifying said ligation product to form ligation amplicons under conditions whereby a fluorescent label is incorporated into said amplicons; and
(d) detecting the presence of said ligation amplicons by detecting the presence of said fluorescent label.

10. A method of claim 9, wherein said target nucleic acid sequence is RNA and/or DNA.

11. A method of claim 9, wherein said target nucleic acid sequence comprises unpurified RNA.

12. A method as in claim 9, wherein said detecting step is by capillary electrophoresis.

\* \* \* \* \*